US012655075B2

(12) United States Patent
Podrebarac et al.

(10) Patent No.: US 12,655,075 B2
(45) Date of Patent: Jun. 16, 2026

(54) METHODS AND SYSTEMS FOR CONVERTING CARBON OXIDES TO OLEFINS

(71) Applicant: Lummus Technology LLC, Houston, TX (US)

(72) Inventors: Gary G. Podrebarac, Friendswood, TX (US); Edward Katende, The Woodlands, TX (US); Zan Liu, Katy, TX (US)

(73) Assignee: LUMMUS TECHNOLOGY LLC, Houston, TX (US)

( * ) Notice: Subject to any disclaimer, the term of this patent is extended or adjusted under 35 U.S.C. 154(b) by 235 days.

(21) Appl. No.: 17/524,925

(22) Filed: Nov. 12, 2021

(65) Prior Publication Data

US 2022/0153657 A1 May 19, 2022

Related U.S. Application Data

(60) Provisional application No. 63/113,636, filed on Nov. 13, 2020, provisional application No. 63/223,215, filed on Jul. 19, 2021.

(51) Int. Cl.
*C07C 1/12* (2006.01)
*C07C 1/04* (2006.01)
(Continued)

(52) U.S. Cl.
CPC .............. *C07C 1/12* (2013.01); *C07C 1/041* (2013.01); *C07C 1/0425* (2013.01); *C07C 1/049* (2013.01); *C07C 1/06* (2013.01); *C25B 1/04* (2013.01)

(58) Field of Classification Search
CPC ......... C07C 1/12; C07C 1/041; C07C 1/0425; C07C 1/049; C07C 1/06; C07C 9/04; C07C 11/04; C07C 9/06; C07C 2/84; C25B 1/04
See application file for complete search history.

(56) References Cited

U.S. PATENT DOCUMENTS

| | | | |
|---|---|---|---|
| 2,324,172 | A | 7/1943 | Parkhurst |
| 2,486,980 | A | 11/1949 | Robinson |
| | (Continued) | | |

FOREIGN PATENT DOCUMENTS

| | | | |
|---|---|---|---|
| CN | 10291237 | B | 4/2015 |
| JP | 2018537532 | A | 12/2018 |
| | (Continued) | | |

OTHER PUBLICATIONS

International Search Report and Written Opinion from PCT/US2021/059077 dated Mar. 8, 2022.
(Continued)

*Primary Examiner* — Jafar F Parsa
(74) *Attorney, Agent, or Firm* — Calfee, Halter & Griswold LLP

(57) ABSTRACT

A method of converting carbon oxides to olefins is provided. The method can include directing a renewable hydrogen feed stream and a carbon oxide feed stream to a methanation reactor to generate an oxidative coupling of methane (OCM) feed stream that includes methane. The OCM feed stream and an oxidant feed stream including oxygen are directed to an OCM reactor containing an OCM catalyst to produce an OCM effluent that includes ethylene. A system for converting carbon oxides to olefins is also provided. The methods and systems produce olefins including ethylene with negative carbon emissions.

19 Claims, 6 Drawing Sheets

500

600

(51) Int. Cl.
    *C07C 1/06*         (2006.01)
    *C25B 1/04*         (2021.01)

(56)            References Cited

U.S. PATENT DOCUMENTS

| | | |
|---|---|---|
| 2,577,701 A | 12/1951 | Philip et al. |
| 2,579,601 A | 12/1951 | Nelson et al. |
| 2,621,216 A | 12/1952 | White |
| 2,643,216 A | 6/1953 | Findlay |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | Armand |
| 3,413,817 A | 12/1968 | Kniel |
| 3,459,678 A | 8/1969 | Hagemeyer, Jr. et al. |
| 3,516,262 A | 6/1970 | Bernstein |
| 3,584,071 A | 6/1971 | McNulty et al. |
| 3,596,473 A | 8/1971 | Streich |
| 3,660,519 A | 5/1972 | Takaaki et al. |
| 3,686,334 A | 8/1972 | Britton |
| 3,686,350 A | 8/1972 | Ono et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Hutson et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,115,086 A | 9/1978 | Jordan et al. |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,418,045 A | 11/1983 | Sato et al. |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,519,824 A | 5/1985 | Huebel |
| 4,523,049 A | 6/1985 | Jones et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,849,575 A | 7/1989 | Lewis |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,889,545 A | 12/1989 | Campbell et al. |
| 4,891,457 A | 1/1990 | Owen et al. |
| 4,895,823 A | 1/1990 | Kolts et al. |
| 4,900,347 A | 2/1990 | Mccue, Jr. et al. |
| 4,935,568 A | 6/1990 | Harandi et al. |
| 4,939,311 A | 7/1990 | Washecheck et al. |
| 4,939,312 A | 7/1990 | Manfred et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,026,934 A | 6/1991 | Bains et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,095,161 A | 3/1992 | Abrevaya et al. |
| 5,113,032 A | 5/1992 | Cameron et al. |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,245,099 A | 9/1993 | Mitariten |
| 5,254,781 A | 10/1993 | Calamur et al. |
| 5,263,998 A | 11/1993 | Mackrodt et al. |
| 5,288,935 A | 2/1994 | Fabio et al. |
| 5,292,979 A | 3/1994 | Chauvin et al. |
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | Mccue et al. |
| 5,430,219 A | 7/1995 | Sanfilippo et al. |
| 5,449,850 A | 9/1995 | Young et al. |
| 5,457,256 A | 10/1995 | Mitariten et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |

(56) References Cited

U.S. PATENT DOCUMENTS

| | | | |
|---|---|---|---|
| 5,659,090 A | 8/1997 | Cameron et al. |
| 5,670,442 A | 9/1997 | Giuseppe et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | Devries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Trubenbach et al. |
| 5,935,898 A | 8/1999 | Trubenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,342,149 B1 | 1/2002 | Koester et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,602,920 B2 | 8/2003 | Hall et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,793,517 B2 | 9/2010 | Patel et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,951,283 B2 | 5/2011 | Stoots et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |

(56) References Cited

U.S. PATENT DOCUMENTS

| | | |
|---|---|---|
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,366,902 B2 | 2/2013 | Hawkes et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild Hansen |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,464,010 B2 | 10/2016 | Naterer et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 * | 2/2017 | Radaelli ................... C07C 1/04 |
| 9,598,328 B2 | 3/2017 | Nyce et al. |
| 9,624,589 B2 | 4/2017 | Rosenthal et al. |
| 9,631,284 B2 | 4/2017 | Braun et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,183,900 B2 | 1/2019 | Nyce et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 | 9/2019 | Radaelli et al. |
| 10,787,398 B2 | 9/2020 | Nyce et al. |
| 10,787,400 B2 | 9/2020 | Radaelli et al. |
| 10,793,490 B2 | 10/2020 | Radaelli et al. |
| 10,988,427 B2 | 4/2021 | Tachibana et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0021379 A1 | 2/2006 | Ronczy |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith, Jr. et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1 | 6/2008 | Bozzano et al. |
| 2008/0194900 A1 | 8/2008 | Bhirud |
| 2008/0207975 A1 | 8/2008 | Crone et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0105066 A1 | 4/2009 | Kang et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2009/0312591 A1 | 12/2009 | Schubert et al. |
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0140144 A1 | 6/2010 | Clinton et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1 | 9/2010 | Butler |
| 2010/0256245 A1 | 10/2010 | Iaccino et al. |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |

(56) References Cited

U.S. PATENT DOCUMENTS

| | | |
|---|---|---|
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0259025 A1* | 10/2012 | Zhao ........................ C25B 1/04 |
| | | 422/162 |
| 2012/0277474 A1 | 11/2012 | Graham Ronald et al. |
| 2012/0302807 A1 | 11/2012 | Elseviers |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045458 A1 | 2/2015 | Zhang et al. |
| 2015/0045599 A1 | 2/2015 | Frey et al. |
| 2015/0065767 A1 | 3/2015 | Henao et al. |
| 2015/0099914 A1 | 4/2015 | Garza et al. |

| | | |
|---|---|---|
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0246856 A1 | 9/2015 | Schmigalle et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long |
| 2016/0272556 A1 | 9/2016 | Rafique et al. |
| 2016/0272557 A1 | 9/2016 | Radaelli et al. |
| 2016/0289143 A1* | 10/2016 | Duggal ..................... C07C 1/12 |
| 2016/0318828 A1 | 11/2016 | Washburn et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0022125 A1 | 1/2017 | Fichtl |
| 2017/0057889 A1 | 3/2017 | Sarsani et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0062642 A1 | 2/2019 | Wei et al. |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0249315 A1 | 8/2019 | Mihalcea et al. |
| 2019/0389788 A1 | 12/2019 | Mamedov et al. |
| 2020/0031734 A1 | 1/2020 | Cizeron et al. |
| 2020/0031736 A1 | 1/2020 | Weinberger et al. |
| 2020/0048165 A1 | 2/2020 | Duggal et al. |
| 2020/0054983 A1 | 2/2020 | Jonnavittula et al. |
| 2020/0055796 A1 | 2/2020 | Nyce et al. |
| 2020/0071242 A1 | 3/2020 | Patel et al. |
| 2020/0131100 A1 | 4/2020 | Schammel et al. |
| 2020/0172452 A1 | 6/2020 | Duggal et al. |
| 2020/0189994 A1 | 6/2020 | Radaelli et al. |
| 2020/0207684 A1 | 7/2020 | Rafique et al. |
| 2020/0207685 A1 | 7/2020 | Nyce et al. |
| 2020/0216370 A1 | 7/2020 | Rafique et al. |
| 2020/0231519 A1 | 7/2020 | Abudawoud et al. |

FOREIGN PATENT DOCUMENTS

| | | | |
|---|---|---|---|
| WO | | 2010107675 A2 | 9/2010 |
| WO | | 2011149996 A2 | 12/2011 |

(56) References Cited

FOREIGN PATENT DOCUMENTS

| WO | 2012162526 A2 | 11/2012 |
|----|---------------|---------|
| WO | 2013106771 A2 | 7/2013 |
| WO | 2013177433 A2 | 11/2013 |
| WO | 2013177461 A2 | 11/2013 |
| WO | 2014011646 A1 | 1/2014 |
| WO | 2014089479 A1 | 6/2014 |
| WO | 2014143880 A1 | 9/2014 |
| WO | 2014154253 A1 | 10/2014 |
| WO | 2015081122 A2 | 6/2015 |
| WO | 2015105911 A1 | 7/2015 |
| WO | 2015106023 A1 | 7/2015 |
| WO | 2016149507 A1 | 9/2016 |
| WO | 2016160563 A1 | 10/2016 |
| WO | 2016205411 A2 | 12/2016 |
| WO | 2017009577 A1 | 1/2017 |
| WO | 2017065947 A1 | 4/2017 |
| WO | 2016205411 A3 | 9/2017 |
| WO | 2017180910 A1 | 10/2017 |
| WO | 2018102601 A1 | 6/2018 |
| WO | 2018118105 A1 | 6/2018 |
| WO | 2018189097 A1 | 10/2018 |
| WO | 2018210782 A1 | 11/2018 |
| WO | 2019010498 A1 | 1/2019 |
| WO | 2019157507 A1 | 8/2019 |
| WO | 2022104015 A1 | 5/2022 |

OTHER PUBLICATIONS

Department of Energy, "Scientists Accidentally Turned CO2 Into Ethanol," Oct. 21, 2016, https://www.energy.gov/articles/scientists-accidentally-turned-co2-ethanol.

Graves, C.R., "Recycling CO2 into Sustainable Hydrocarbon Fuels: Electrolysis of CO2 and H2O," Dissertation, Columbia University (2010).

Green Car Congress, "ReactWell licenses ORNL catalyst for direct conversion of CO2 to ethanol," Mar. 8, 2019, https://www.greencarcongress.com/2019/03/20190308-reactwell.html.

Tian Qin et al., "Enhanced Electrochemical Reduction of CO2 to Ethylene on Electrodeposited Copper in 0.1 M KHCO3," International Journal of Electrochemical Science, vol. 13 (2018), pp. 10101-10112.

Water Electrolysis & Renewable Energy Systems. FuelCellToday (May 2013).

Gao et al., "Direct and Selective Hydrogenation of CO2 to Ethylene and Propene by Bifunctional Catalysts," Catalysis Science & Technology, Issue 23 (2017) pp. 5602-5607.

Ren et al., "Olefins from conventional and heavy feedstocks: Energy use in steam cracking and alternative processes," Energy, vol. 31, Issue 4, Mar. 2006, pp. 425-451.

Carneiro et al., "Electrochemical Reduction of CO2 on Metal-Based Cathode Electrocatalysts of Solid Oxide Electrolysis Cells," Industrial & Engineering Chemistry Research (2020), vol. 59, pp. 15884-15893.

Fu et al., "Syngas production via high-temperature steam/CO2 co-electrolysis: an economic assessment," Energy Environ. Sci. (2010), vol. 3, pp. 1382-1397.

Gao et al., "Intensified co-electrolysis process for syngas production from captured CO2," Journal of CO2 Utilization (2021), vol. 43, 101365 (available online Nov. 25, 2020).

Kungas, Rainer, "Review—Electrochemical CO2 Reduction for CO Production: Comparison of Low- and High-Temperature Electrolysis Technologies," Journal of the Electrochemical Society (2020), vol. 167, No. 4, 044508.

Lu et al., "Electrosynthesis of Syngas via the Co-Reduction of CO2 and H2O," Cell Reports Physical Science, vol. 1, 100237 (Nov. 18, 2020).

Zhan et al., "Syngas Production by Coelectrolysis of CO2/H2O: The Basis for a Renewable Energy Cycle," Energy & Fuels (2009), vol. 23, pp. 3089-3096.

Zhao et al., "An economic analysis of twenty light olefin production pathways," Journal of Energy Chemistry, vol. 56 (2021) pp. 193-202.

Office Action from CA Application No. 3,138,540 dated Nov. 8, 2023.

Office Action from CA Application No. 3, 138,540 dated Aug. 7, 2025.

Office Action from CN Application No. 202180006106.0 dated Jul. 10, 2025.

Office Action from IL Application No. 288058 dated Feb. 15, 2024.

Office Action from JP Application No. 2023-553159 dated Jun. 2, 2025.

Office Action from KZ Application No. 2023/0405.1 received on Aug. 16, 2024.

Office Action from KZ Application No. 2023/0405.1 received on Jun. 9, 2025.

Office Action from TW Application No. 110142135 dated Apr. 22, 2025.

Office Action from TW Application No. 110142135 dated Dec. 19, 2025.

Office Action from JP Application No. 2023-553159 dated Mar. 2, 2026.

* cited by examiner

500

METHODS AND SYSTEMS FOR CONVERTING CARBON OXIDES TO OLEFINS

CROSS-REFERENCE TO RELATED APPLICATIONS

This application claims priority to and the benefit of U.S. Provisional Patent Application No. 63/113,636, filed Nov. 13, 2020, and U.S. Provisional Patent Application No. 63/223,215, filed Jul. 19, 2021, the entire contents of which are incorporated by reference herein.

FIELD

The present disclosure relates to methods and systems for converting carbon oxides to olefins. More particularly, the present disclosure relates to methods and systems for converting carbon oxides to ethylene with negative carbon emissions.

BACKGROUND

The production of olefins generally results in the release of very significant amounts of carbon dioxide ($CO_2$) into the atmosphere. Indeed, steam cracking of saturated hydrocarbons to produce olefins is one of the most energy consuming processes in the chemical industry. It has been reported that the production of one ton of olefins (i.e., a mix of ethylene and propylene) results in the emission of nearly one ton of $CO_2$. There is growing pressure around the world to reduce the emission of greenhouse gases and, more particularly, to reduce the emission of $CO_2$.

Several methods of producing ethylene ($C_2H_4$) from $CO_2$ have been suggested. In one method, the first step is to use the Sabatier methanation reaction to convert $CO_2$ into methane ($CH_4$). The next step is to steam reform the $CH_4$ to produce syngas (i.e., CO and $H_2$). In a subsequent step, the syngas is used to produce methanol ($CH_3OH$). Finally, the $CH_3OH$ is converted to light olefins (e.g., $C_2H_4$) and water using a zeolite catalyst. This particular method of producing $C_2H_4$ involves many steps and constructing such a plant to perform the process would be cost prohibitive. Another issue with this particular method involves the source of hydrogen ($H_2$) that would be used for methanation. Because steam reforming of methane is the major source of $H_2$, this particular method would produce more $CO_2$ than it would consume.

Another method of producing $C_2H_4$ from $CO_2$ performs a methanol synthesis reaction and conversion of the synthesized $CH_3OH$ to olefins in the same reactor, which would bypass the steam reforming step and reduce the cost of the plant (Gao et al., *Catalysis Science and Technology* (2017), Vol. 23, 5602-5607). This method involves using a methanol synthesis catalyst in an upper catalyst bed of the reactor that converts $CO_2$ and $H_2$ directly into $CH_3OH$ and using a methanol-to-olefins catalyst (e.g., SAPO-34) in a lower catalyst bed of the reactor to convert the $CH_3OH$ into light olefins and water.

In addition, an electrochemical technique has been suggested to convert $CO_2$ into $C_2H_4$ (See Qin et al., *Int. J. Electrochem. Sci.* (2018), Vol. 13, 10101-10112). Another electrochemical technique involves the conversion of $CO_2$ into ethanol using a catalyst made of carbon, copper and nitrogen (https://www.energy.gov/articles/scientists-accidentally-turned-co2-ethanol). The ethanol can then be converted to $C_2H_4$ via a dehydration reaction.

Thermochemical cycles have also been suggested as a way to convert $CO_2$ into useful products. U.S. Pat. No. 9,464,010 discloses the use of a copper-chlorine (Cu—Cl) thermochemical cycle as a way to generate $H_2$ needed to capture and convert $CO_2$ into useful products.

While several processes have been suggested for converting $CO_2$ to olefins, these processes are generally too expensive to be practical or are many years away from commercialization. In addition, some of these processes generate more $CO_2$ than they consume, while some of the processes involving $CH_3OH$ as an intermediate do not utilize the $O_2$ that is produced.

SUMMARY

Disclosed herein are methods and systems for converting carbon oxides to olefins, particularly ethylene, that utilize renewable hydrogen and reduce greenhouse gas emissions. In addition, the methods and systems for converting carbon oxides to olefins have a high carbon efficiency and achieve negative carbon emissions.

In accordance with the invention of the present disclosure, a method of converting carbon oxides to olefins including ethylene ($C_2H_4$) is provided. The method includes directing a renewable hydrogen ($H_2$) feed stream and a carbon oxide feed stream comprising carbon dioxide ($CO_2$), carbon monoxide (CO), or both $CO_2$ and CO to a methanation reactor to generate an oxidative coupling of methane (OCM) feed stream comprising methane ($CH_4$). The OCM feed stream and an oxidant feed stream comprising oxygen ($O_2$) are directed to an OCM reactor comprising an OCM catalyst. An OCM reaction is performed to generate an OCM effluent comprising (i) $C_{2+}$ compounds including $C_2H_4$ and ethane ($C_2H_6$) and (ii) non-$C_{2+}$ impurities comprising one or more of CO, $CO_2$, $H_2$, and $CH_4$. The method produces olefins including $C_2H_4$ with negative carbon emissions.

In accordance with the invention of the present disclosure, a method of converting $CO_2$ to olefins including $C_2H_4$ is provided. The method includes directing a natural gas stream containing $CO_2$ to a gas treatment unit to generate a $CO_2$ feed stream and a substantially $CO_2$-free natural gas stream. The $CO_2$ feed stream and a renewable $H_2$ feed stream are directed to a methanation reactor to generate an OCM feed stream comprising $CH_4$. The OCM feed stream and an oxidant feed stream comprising oxygen $O_2$ are directed to an OCM reactor comprising an OCM catalyst. An OCM reaction is performed to generate an OCM effluent comprising (i) $C_{2+}$ compounds including $C_2H_4$ and $C_2H_6$ and (ii) non-$C_{2+}$ impurities comprising one or more of CO, $CO_2$, $H_2$, and $CH_4$. The method produces olefins including $C_2H_4$ with negative carbon emissions.

In accordance with the invention of the present disclosure, a system for converting carbon oxides to olefins including $C_2H_4$ is provided. The system includes a renewable hydrogen ($H_2$) subsystem configured to generate a renewable $H_2$ feed stream. A methanation subsystem is located downstream of and fluidly coupled to the renewable $H_2$ subsystem. The methanation subsystem is configured to receive the renewable $H_2$ feed stream and a carbon oxide feed stream comprising $CO_2$, CO, or both $CO_2$ and CO and to generate an OCM feed stream comprising methane $CH_4$. An OCM subsystem is located downstream of and fluidly coupled to the methanation subsystem. The OCM subsystem is configured to receive the OCM feed stream and an oxidant feed stream comprising $O_2$ and to generate an OCM effluent comprising (i) $C_{2+}$ compounds including $C_2H_4$ and $C_2H_6$ and (ii) non-$C_{2+}$ impurities comprising one or more of CO, $CO_2$, $H_2$, and $CH_4$. The system also includes a separations subsystem downstream of and fluidly coupled to the OCM subsystem. The separations subsystem is configured to receive the OCM effluent and to separate the OCM effluent into at least (i) a first stream comprising $CO_x$, $H_2$, and $CH_4$ and (ii) a second stream comprising $C_{2+}$ compounds including $C_2H_4$ and $C_2H_6$. The system is configured to operate such that olefins including $C_2H_4$ are produced with negative carbon emissions.

In accordance with the invention of the present disclosure, a method of converting $CO_2$ to olefins including ethylene ($C_2H_4$) is provided. The method includes directing a feed stream comprising $CO_2$ to a $CO_2$ electrolysis unit to generate a first renewable electrolysis stream comprising CO and a second renewable electrolysis stream comprising $O_2$. A renewable $H_2$ feed stream and the first renewable electrolysis stream are directed to a methanation reactor to generate an OCM feed stream comprising $CH_4$. The OCM feed stream and an oxidant feed stream comprising the second renewable electrolysis stream are directed to an OCM reactor comprising an OCM catalyst. An OCM reaction is performed to generate an OCM effluent comprising (i) $C_{2+}$ compounds including $C_2H_4$ and ethane ($C_2H_6$) and (ii) non-$C_{2+}$ impurities comprising one or more of CO, $CO_2$, $H_2$, and $CH_4$. The method produces olefins including $C_2H_4$ with negative carbon emissions.

In accordance with the invention of the present disclosure, a method of converting $CO_2$ to olefins including ethylene ($C_2H_4$) is provided. The method includes directing a first feed stream comprising $CO_2$ and a second feed stream comprising water ($H_2O$) to a co-electrolysis unit to generate a renewable syngas stream comprising CO and $H_2$ and a renewable oxidant stream comprising $O_2$. The renewable syngas stream is directed to a methanation reactor to generate an OCM feed stream comprising $CH_4$. The OCM feed stream and the renewable oxidant stream are directed to an OCM reactor comprising an OCM catalyst. An OCM reaction is performed to generate an OCM effluent comprising (i) $C_{2+}$ compounds including $C_2H_4$ and $C_2H_6$ and (ii) non-$C_{2+}$ impurities comprising one or more of CO, $CO_2$, $H_2$, and $CH_4$. The method produces olefins including $C_2H_4$ with negative carbon emissions.

In accordance with the invention of the present disclosure, a system for converting $CO_2$ to olefins including $C_2H_4$ is provided. The system includes a renewable hydrogen ($H_2$) subsystem configured to generate a renewable $H_2$ feed stream and a $CO_2$ electrolysis unit configured to receive a feed stream comprising $CO_2$ and to generate a first renewable electrolysis stream comprising CO and a second renewable electrolysis stream comprising $O_2$. A methanation subsystem is located downstream of and fluidly coupled to the renewable $H_2$ subsystem and the $CO_2$ electrolysis unit. The methanation subsystem is configured to receive the renewable $H_2$ feed stream and the first renewable electrolysis stream and to generate an OCM feed stream comprising methane $CH_4$. An OCM subsystem is located downstream of and fluidly coupled to the methanation subsystem and the $CO_2$ electrolysis unit. The OCM subsystem is configured to receive the OCM feed stream and an oxidant feed stream comprising the second renewable oxidant stream and to generate an OCM effluent comprising (i) $C_{2+}$ compounds including $C_2H_4$ and $C_2H_6$ and (ii) non-$C_{2+}$ impurities comprising one or more of CO, $CO_2$, $H_2$, and $CH_4$. The system also includes a separations subsystem downstream of and fluidly coupled to the OCM subsystem. The separations subsystem is configured to receive the OCM effluent and to separate the OCM effluent into at least (i) a first stream comprising $CO_x$, $H_2$, and $CH_4$ and (ii) a second stream comprising $C_{2+}$ compounds including $C_2H_4$ and $C_2H_6$. The system is configured to operate such that olefins including $C_2H_4$ are produced with negative carbon emissions.

In accordance with the invention of the present disclosure, a system for converting $CO_2$ to olefins including $C_2H_4$ is provided. The system includes a co-electrolysis unit configured to receive a first feed stream comprising $CO_2$ and a second feed stream $H_2O$ and to generate a renewable syngas stream comprising CO and $H_2$ and a renewable oxidant stream comprising $O_2$. A methanation subsystem is located downstream of and fluidly coupled to the co-electrolysis unit. The methanation subsystem is configured to receive the renewable syngas stream and to generate an OCM feed stream comprising methane $CH_4$. An OCM subsystem is located downstream of and fluidly coupled to the methanation subsystem and the co-electrolysis unit. The OCM subsystem is configured to receive the OCM feed stream and the renewable oxidant stream and to generate an OCM effluent comprising (i) $C_{2+}$ compounds including $C_2H_4$ and $C_2H_6$ and (ii) non-$C_{2+}$ impurities comprising one or more of CO, $CO_2$, $H_2$, and $CH_4$. The system also includes a separations subsystem downstream of and fluidly coupled to the OCM subsystem. The separations subsystem is configured to receive the OCM effluent and to separate the OCM effluent into at least (i) a first stream comprising $CO_x$, $H_2$, and $CH_4$ and (ii) a second stream comprising $C_{2+}$ compounds including $C_2H_4$ and $C_2H_6$. The system is configured to operate such that olefins including $C_2H_4$ are produced with negative carbon emissions.

Other aspects and advantages of the present disclosure will be apparent from the description that follows.

DETAILED DESCRIPTION

Figure 1:
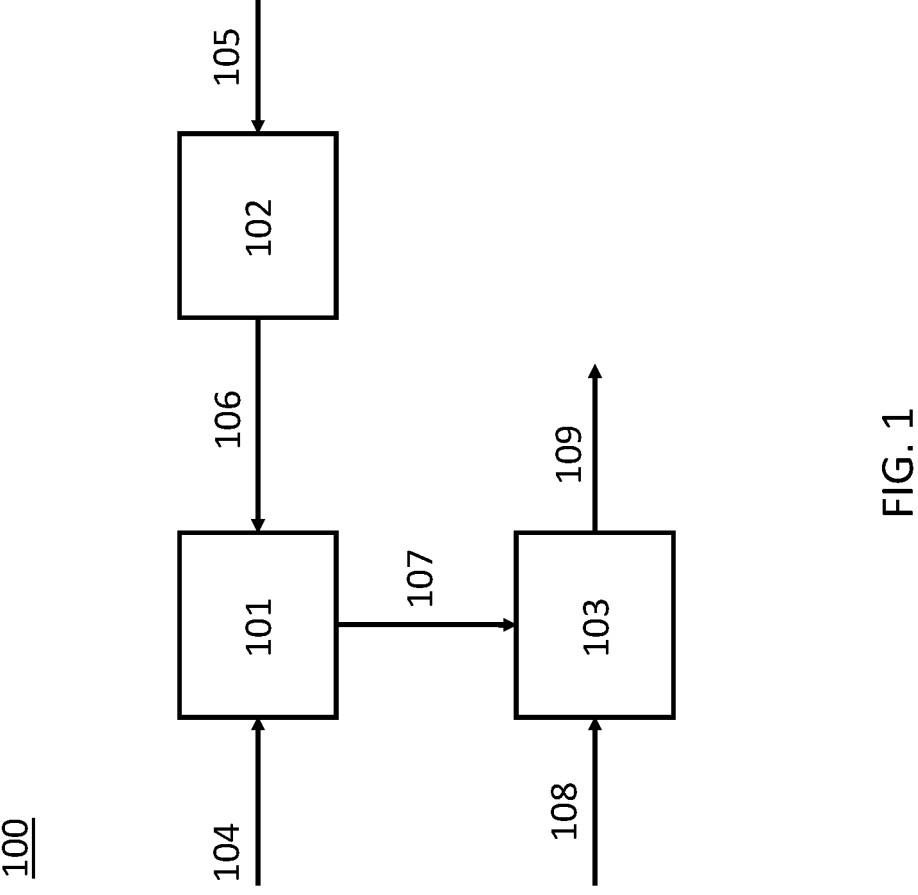
FIG. 1 illustrates a block flow diagram of a system for producing olefins, such as ethylene, from a carbon oxide feed stream in accordance with the present disclosure.

Described herein are methods and systems for converting carbon oxides to olefins. In accordance with the invention of the present disclosure, a carbon oxide feed stream is a primary or sole source of carbon fed into the process or system, along with a renewable hydrogen ($H_2$) feed stream and an oxidant feed stream comprising oxygen ($O_2$), to produce olefins, including ethylene ($C_2H_4$). The olefins are produced via an oxidative coupling of methane (OCM) reaction. In accordance with the invention of the present disclosure, the methods and systems for converting carbon oxides to olefins can: (i) reduce or eliminate greenhouse gas emissions associated with the production of olefins; (ii) operate at a high carbon efficiency (i.e., greater than 90%); and/or (iii) produce olefins with negative carbon emissions.

The term "OCM reaction," as used herein, generally refers to an oxidative coupling of methane reaction or process to produce ethylene ($C_2H_4$). An OCM reaction can include the oxidation of methane to a hydrocarbon and water and involves an exothermic reaction. In an OCM reaction, methane can be partially oxidized to one or more $C_{2+}$ compounds, such as ethylene. In an example, an OCM reaction is $2 CH_4+O_2 \rightarrow C_2H_4+2 H_2O$. An OCM reaction can yield $C_{2+}$ compounds. An OCM reaction can be facilitated by an OCM catalyst, such as a heterogeneous catalyst. Additional by-products of OCM reactions can include CO, $CO_2$, and $H_2$. Ethane can also react to form ethylene over the OCM catalyst in an OCM reaction.

The terms "$C_{2+}$" and "$C_{2+}$ compound," as used herein, generally refer to a compound comprising two or more carbon atoms, e.g., $C_2$, $C_3$, etc. $C_{2+}$ compounds include, without limitation, alkanes, alkenes, alkynes, aldehydes, ketones, aromatics esters, and carboxylic acids containing two or more carbon atoms. Examples of $C_{2+}$ compounds include ethane, ethylene, ethyne, propane, propylene, propyne, and so forth. Similarly, the terms "$C_{3+}$" and "$C_{3+}$ compound," as used herein generally refer to a compound comprising three or more carbon atoms, e.g., $C_3$, $C_4$, $C_5$, etc. $C_{3+}$ compounds include, without limitation, alkanes, alkenes, alkynes, aldehydes, ketones, aromatics esters, and carboxylic acids containing two or more carbon atoms. Examples of $C_{3+}$ compounds include propane, propylene, propyne, butane, butene, and so forth.

The term "non-$C_{2+}$ impurities," as used herein, generally refers to material that does not include $C_{2+}$ compounds. Examples of non-$C_{2+}$ impurities, which may be found in certain OCM reaction product streams include, but are not limited to, nitrogen ($N_2$), oxygen ($O_2$), water ($H_2O$), argon (Ar), hydrogen ($H_2$) carbon monoxide (CO), carbon dioxide ($CO_2$), and methane ($CH_4$).

The term "carbon efficiency," as used herein, generally refers to the ratio of the number of moles of carbon present in all process input streams (in some cases including all hydrocarbon feedstocks, such as, e.g., natural gas and ethane and fuel streams) to the number of moles of carbon present in all commercially (or industrially) usable or marketable products of the process. Such products can include hydrocarbons that can be employed for various downstream uses, such as petrochemical or for use as commodity chemicals. Such products can exclude CO and $CO_2$. The products of the process can be marketable products, such as $C_{2+}$ hydrocarbon products containing at least about 99% $C_{2+}$ hydrocarbons and all sales gas or pipeline gas products containing at least about 90% methane. Process input streams can include input streams providing power for the operation of the process. In some cases, at least a portion of the power for the operation of the process can be provided by heat liberated by an OCM reaction.

The term "$CO_x$," as used herein, refers to carbon monoxide (where x=1), carbon dioxide (where x=2), or both carbon monoxide and carbon dioxide.

The term "unit," as used herein, generally refers to a unit operation. A unit operation may be one or more basic operations in a process. A unit may have one or more sub-units (or subsystems). Unit operations may involve a physical change or chemical transformation, such as separation, crystallization, evaporation, filtration, polymerization, isomerization, other reactions, or combinations thereof. A unit may include one or more individual components. For example, a separations unit may include one or more separation columns or an amine unit may include one or more amine columns.

The terms "olefin" and "alkene" are used interchangeably herein and generally refer to a hydrocarbon containing one or more double bonds.

The terms "adiabatic" or "adiabatic process," generally refer to a process in which the pressure of a gas may be allowed to increase without substantial heat losses to the surroundings. An adiabatic unit or element may permit little to no heat transfer between units or elements, such as, for example, less than 15%, 10%, 5%, 4%, 3%, 2%, or 1% heat transfer (e.g., as measured by total heat input and heat output from the unit).

The term "substantially $CO_2$-free," as used herein, generally refers to a $CO_2$ molar percentage of less than 1%, including less than 0.5%, less than 0.25%, less than 0.1%, less than 0.05%, and also including 0%.

In accordance with the present invention, it has been discovered that olefins, including $C_2H_4$, can be produced by methods and systems that utilize a carbon oxide feed stream as a primary or sole source of carbon fed into the process or system along with a renewable $H_2$ feed stream and an oxidant feed stream comprising $O_2$. The methods and systems disclosed herein also utilize a methanation reaction and an oxidative coupling of methane (OCM) reaction to produce the olefins. The methods and systems of the present disclosure have several advantages over known OCM methods and systems including the reduction or elimination of greenhouse gas emissions (e.g., $CO_2$), the ability to operate at a high carbon efficiency, and the ability to produce olefins, including $C_2H_4$, with negative carbon emissions.

Reference will now be made to the figures to further describe the methods and systems of the present disclosure. It will be appreciated that the figures and features therein are not necessarily drawn to scale. In the figures, the direction of fluid flow between units is indicated by arrows. Fluid may be directed from one unit to another with the aid of valves and a fluid flow system. As those of skill in the art will appreciate, such fluid flow systems may include compressors and/or pumps, as well as a control system for regulating fluid flow.

Referring now to FIG. 1, a block flow diagram of a system 100 for performing a method of converting carbon oxides to olefins, including $C_2H_4$, in accordance with the present invention is shown. The system 100 comprises a methanation subsystem 101, a renewable $H_2$ subsystem 102, and an OCM subsystem 103. The methanation subsystem 101 is fluidly coupled to the renewable $H_2$ subsystem 102 and is configured to receive a carbon oxide feed stream 104 and a renewable $H_2$ feed stream 106 generated by the renewable $H_2$ subsystem 102 to generate an OCM feed stream 107 comprising $CH_4$. The OCM subsystem 103 is downstream of and fluidly coupled to the methanation subsystem 101 and is configured to receive the OCM feed stream 107 and an oxidant feed stream 108 comprising $O_2$ to generate an OCM effluent 109 comprising $C_{2+}$ compounds including $C_2H_4$ and $C_2H_6$ and non-$C_{2+}$ impurities comprising one or more of CO, $CO_2$, $H_2$, and $CH_4$.

The methanation subsystem 101 can include one or more methanation reactors that contain a methanation catalyst (e.g., a nickel-based catalyst) for carrying out a methanation reaction. The typical operating conditions of a methanation reactor can be at a pressure of about 3 bar to about 50 bar and a temperature of about 150° C. to about 400° C. In the methanation subsystem 101, the carbon oxides (e.g., $CO_2$, CO, or both) in the carbon oxide feed stream 104 react with the $H_2$ from the renewable $H_2$ feed stream 106 to produce $CH_4$ via the following reactions: i) $CO_2+4\ H_2\rightarrow CH_4+2\ H_2O$ and ii) $CO+3\ H_2\rightarrow CH_4+H_2O$. The $CH_4$ generated in the methanation subsystem 101 is directed to the OCM subsystem 103 as the OCM feed stream 107.

In accordance with the methods and systems of the present disclosure, the carbon oxide feed stream 104 comprises $CO_2$, CO, or both $CO_2$ and CO. In accordance with the methods and systems of the present disclosure, the carbon oxide feed stream 104 is a primary or sole source of carbon fed into the system 100 or process. In accordance with some aspects of the methods and systems of the present disclosure, the carbon oxide feed stream 104 comprises captured $CO_2$. The captured $CO_2$ may be $CO_2$ that is captured from industrial facilities including, but not limited to, steel/metal production facilities, cement production facilities, coal-fired power plants, coal gasification, and biomass gasification. The captured $CO_2$ may also include some amount of CO. In accordance with some aspects of the methods and systems of the present disclosure, the carbon oxide feed stream 104 comprises a $CO_2$ feed stream that is generated by removing $CO_2$ from a natural gas stream containing $CO_2$. In accordance with some aspects of the methods and systems of the present disclosure, the carbon oxide feed stream 104 comprises captured $CO_2$ (e.g., $CO_2$ captured from industrial facilities), which may include some amount of CO, and $CO_2$ that is generated by removing $CO_2$ from a natural gas stream containing $CO_2$.

The renewable $H_2$ feed stream 106 directed to the methanation subsystem 101 is generated by the renewable $H_2$ subsystem 102. In accordance with the methods and systems of the present disclosure, the renewable $H_2$ subsystem 102 may be based on one or more technologies for generating renewable $H_2$. Such technologies include, but are not limited to, water electrolysis, biomass gasification, ammonia cracking, and hydrogen sulfide decomposition. The energy required to power the renewable $H_2$ subsystem 102 to generate the renewable $H_2$ feed stream 106 may be provided by one or more renewable energy sources. Exemplary renewable energy sources that may be used in accordance with the methods and systems of the present disclosure include, but are not limited to, wind, solar, biomass, geothermal, hydro-electric, and nuclear.

As seen in FIG. 1, a $H_2$ carrier stream 105 is directed to the renewable $H_2$ subsystem 102 to generate a renewable $H_2$ feed stream 106 that is directed to the methanation subsystem 101. In accordance with the methods and systems of the present disclosure, the $H_2$ carrier stream 105 comprises a $H_2$ carrier. The $H_2$ carrier may be any compound or substance that can be treated (e.g., reacted, decomposed) to produce $H_2$ gas. Examples of $H_2$ carriers suitable for use in the methods and systems of the present disclosure include, but are not limited to, water, biomass, ammonia, and hydrogen sulfide.

With continued reference to FIG. 1, the OCM feed stream 107 generated by the methanation subsystem 101 is directed to the OCM subsystem 103 along with the oxidant feed stream 108 to produce the OCM effluent 109. As described in more detail herein, the OCM effluent 109 can be directed to downstream units and/or a separations subsystem for additional processing of the OCM effluent 109. The oxidant feed stream 108 supplied to the OCM subsystem 103 may be provided by any suitable source of $O_2$. In accordance with some aspects of the present disclosure, the OCM feed stream 107 and the oxidant feed stream 108 may be heated prior to being injected into the OCM subsystem 103. Although FIG. 1 illustrates the OCM feed stream 107 and the oxidant feed stream 108 being directed to the OCM subsystem 103 as separate streams, it is contemplated that the OCM feed stream 107 and the oxidant feed stream 108 can be combined and mixed to form a single stream that is directed to the OCM subsystem 103. In accordance with some aspects of the present disclosure, the oxidant feed stream 108 can be provided by an air stream or an $O_2$ stream that is generated by an air separation unit or that is generated by the renewable $H_2$ subsystem 102, a $CO_2$ electrolysis unit, or a co-electrolysis unit as described herein below.

In accordance with the methods and systems of the present disclosure, the OCM subsystem 103 can include one or more OCM reactors in series and/or parallel. The OCM reactors include one or more OCM catalysts for facilitating an OCM reaction to generate the OCM effluent 109 comprising $C_{2+}$ compounds including $C_2H_4$ and $C_2H_6$ and non-$C_{2+}$ impurities comprising one or more of CO, $CO_2$, $H_2$, and $CH_4$. The OCM reactors can operate under isothermal or adiabatic conditions to carry out the OCM reaction. In some aspects of the methods and systems of the present disclosure, an inlet temperature of the OCM reactor can be about 400° C. to about 600° C. and an outlet temperature of the OCM reactor can be about 700° C. to about 900° C. In some aspects of the methods and systems of the present disclosure, an inlet pressure of the OCM reactor is from about 15 pounds per square inch gauge (psig) to about 150 psig. The OCM catalyst may be any known OCM catalyst, such as OCM catalysts designed to operate in low temperature environments (i.e., from about 400° C. to about 600° C.) like the catalysts described in, for example, U.S. Pat. Nos. 8,921,256, 8,962,517, and 9,718,054, the full disclosures of which are incorporated herein by reference in their entirety.

In accordance with the methods and systems of the present disclosure, the OCM subsystem 103 can include a post-bed cracking (PBC) unit for generating olefins (e.g., $C_2H_4$) from alkanes (e.g., $C_2H_6$, $C_3H_8$). The PBC unit can be disposed downstream of the OCM reactor, particularly the OCM catalyst contained in the OCM reactor. The PBC unit may be a separate reactor, or the PBC unit may be included as a section of the OCM reactor (e.g., an OCM catalyst bed disposed upstream of a PBC unit in the same reactor vessel). As the OCM reaction is exothermic and generates heat, the heat generated by the OCM reaction can be used to crack alkanes (e.g., $C_2H_6$) to olefins (e.g., $C_2H_4$). The PBC unit may perform the cracking at a temperature of about 600° C. to about 1,000° C., including a temperature of about 800° C. to about 950° C.

In accordance with the methods and systems of the present disclosure, the PBC unit can be used to crack additional external alkanes (e.g., $C_2H_6$, $C_3H_8$) beyond those contained in the OCM effluent 109. The heat capacity in the OCM effluent 109 can be sufficient to crack some amount of additional external alkanes. The additional external alkanes can be provided from a recycle stream of the process or an entirely separate source of alkanes. The external alkanes can be heated prior to injection into the PBC unit. The external alkanes can be heated by, for example, heat exchange with the OCM reactor and/or the OCM effluent 109.

Figure 2:
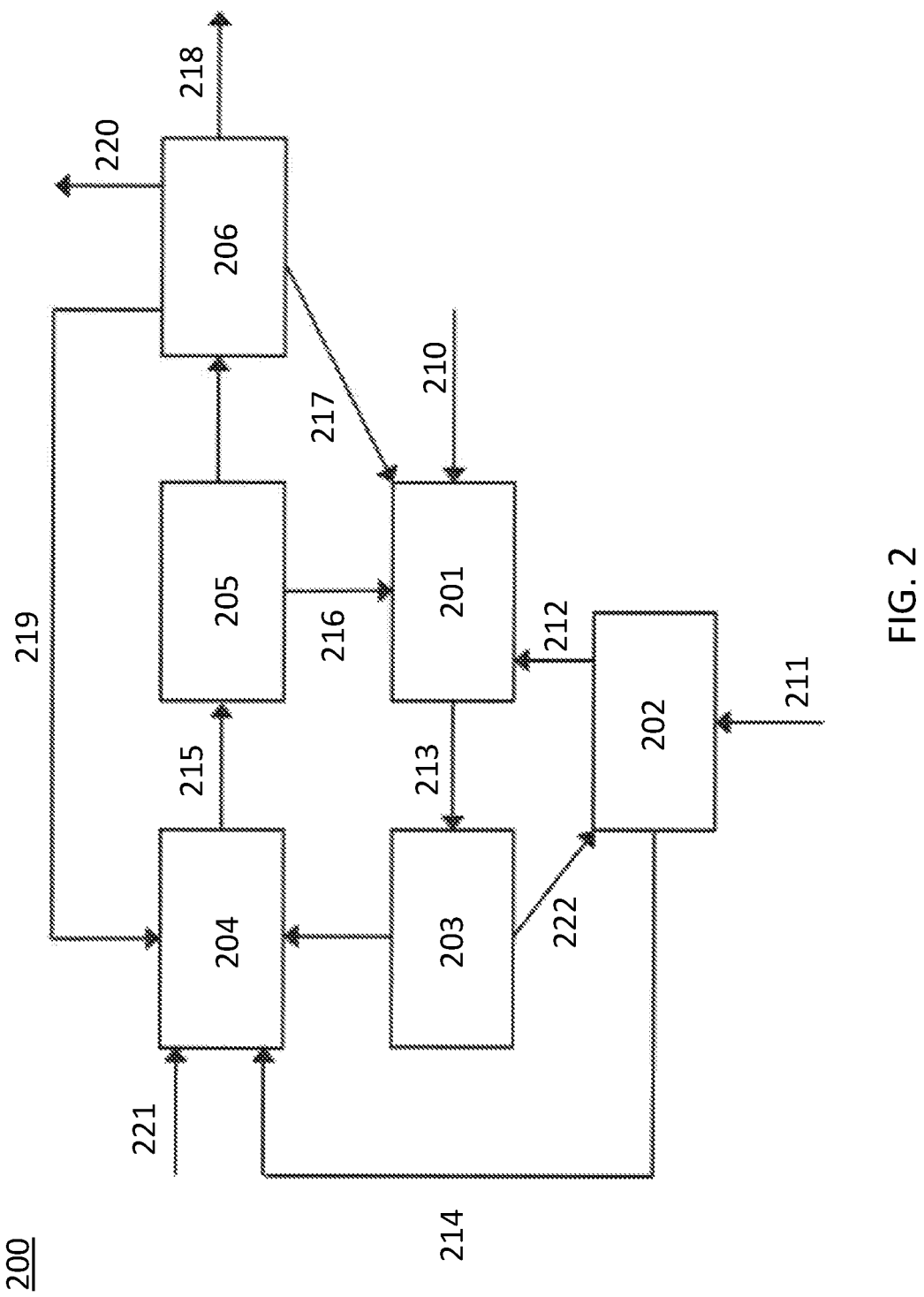
FIG. 2 illustrates a block flow diagram of a system for producing olefins, such as ethylene, from a carbon oxide feed stream in accordance with the present disclosure.

Referring now to FIG. 2, a block flow diagram of a system 200 for performing a method of converting carbon oxides to olefins, including $C_2H_4$, in accordance with the present invention is shown. The system 200 comprises a methanation subsystem 201, a renewable $H_2$ subsystem 202, an OCM subsystem 204, and a separations subsystem 206. The methanation subsystem 201 is fluidly coupled to the renewable $H_2$ subsystem 202 and is configured to receive a carbon oxide feed stream 210 and a renewable $H_2$ feed stream 212 generated by the renewable $H_2$ subsystem 202 and to generate an OCM feed stream 213 comprising $CH_4$. The OCM subsystem 204 is downstream of and fluidly coupled to the methanation subsystem 201 and is configured to receive the OCM feed stream 213 and an oxidant feed stream 214 comprising $O_2$ to generate an OCM effluent 215 comprising $C_{2+}$ compounds including $C_2H_4$ and $C_2H_6$ and non-$C_{2+}$ impurities comprising one or more of CO, $CO_2$, $H_2$, and $CH_4$. The separations subsystem 206 is downstream of and fluidly coupled to the OCM subsystem 204 and is configured to receive the OCM effluent 215 and to separate the OCM effluent 215 into at least a first stream 217 comprising $CO_x$, $H_2$, and $CH_4$ and a second stream comprising $C_{2+}$ compounds including $C_2H_4$ and $C_2H_6$. The second stream may be further separated in the separations subsystem 206 to produce a third stream 218 comprising $C_2H_4$ and a fourth stream 219 comprising $C_2H_6$.

In the system 200 illustrated in FIG. 2, the methanation subsystem 201, the renewable $H_2$ subsystem 202, and the OCM subsystem 204 may be configured the same as the methanation subsystem 101, the renewable $H_2$ subsystem 102, and the OCM subsystem 103 previously described with reference to FIG. 1.

As shown in FIG. 2, a carbon oxide feed stream 210 is directed to the methanation subsystem 201 along with a renewable $H_2$ feed stream 212 generated by the renewable $H_2$ subsystem 202. In accordance with the methods and systems of the present disclosure, the carbon oxide feed stream 210 comprises $CO_2$, CO, or both $CO_2$ and CO. In accordance with the methods and systems of the present disclosure, the carbon oxide feed stream 210 is a primary or sole source of carbon fed into the system 200 or process. In accordance with some aspects of the methods and systems of the present disclosure, the carbon oxide feed stream 210 comprises captured $CO_2$. The captured $CO_2$ may be $CO_2$ that is captured from industrial facilities including, but not limited to, steel/metal production facilities, cement production facilities, coal-fired power plants, coal gasification, and biomass gasification. The captured $CO_2$ may also include some amount of CO.

Figure 3:
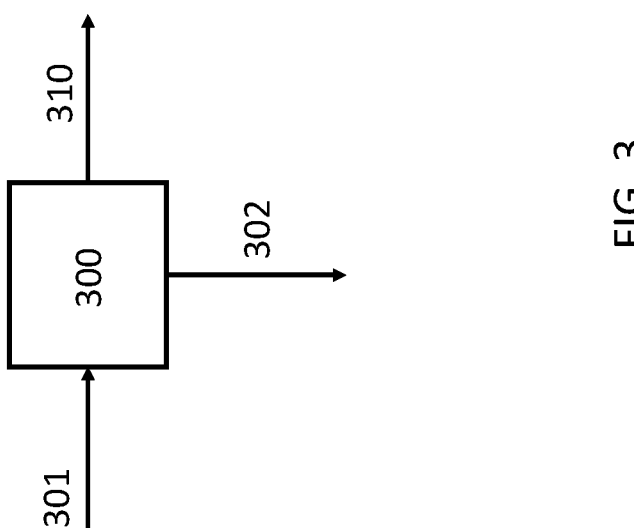
FIG. 3 illustrates a block flow diagram of a gas treatment unit for producing a carbon dioxide feed stream in accordance with the present disclosure.

With reference now to FIGS. 2 and 3, in accordance with some aspects of the methods and systems of the present disclosure, the carbon oxide feed stream 210 may comprise a $CO_2$ feed stream 310 that is generated by removing $CO_2$ from a natural gas stream 301 containing $CO_2$. As shown in FIG. 3, a natural gas stream containing $CO_2$ is directed to a gas treatment unit 300 that is configured to remove $CO_2$ from the natural gas and thereby generate a $CO_2$ feed stream and a substantially $CO_2$-free natural gas stream 302. In accordance with some aspects of the present disclosure, the substantially $CO_2$-free natural gas stream 302 may be exported to a natural gas pipeline (e.g., to be sold as sales gas into the natural gas infrastructure). In accordance with some aspects of the methods and systems of the present disclosure, at least a portion of the substantially $CO_2$-free natural gas stream 302 may be directed to the OCM subsystem 204 as a makeup stream 221 comprising $CH_4$.

The natural gas stream 301 may include any concentration of $CO_2$. In some aspects of the methods and systems of the present disclosure, the natural gas stream 301 may include up to 50 wt. % $CO_2$, including from 1 wt. % to 50 wt. %, from 5 wt. % to 50 wt. %, from 10 wt. % to 50 wt. %, from 15 wt. % to 50 wt. %, from 20 wt. % to 50 wt. %, from 25 wt. % to 50 wt. %, from 30 wt. % to 50 wt. %, from 35 wt. % to 50 wt. %, from 40 wt. % to 50 wt. %, and also including from 45 wt. % to 50 wt. % $CO_2$. In accordance with some aspects of the methods and systems of the present disclosure, the $CO_2$ feed stream 310 comprises at least a portion of the carbon oxide feed stream 210 directed to the methanation subsystem 201, with the remaining portion supplied by captured $CO_2$ as described above. In accordance with some aspects of the methods and systems of the present disclosure, the carbon oxide feed stream 210 directed to the methanation subsystem 201 consists of the $CO_2$ feed stream 310 generated by the gas treatment unit 300.

The gas treatment unit 300 may comprise any conventional system or method known for removing $CO_2$ from natural gas. For example, in some aspects of the methods and systems of the present disclosure, the gas treatment unit 300 may be a natural gas processing plant or a portion thereof. In other aspects of the methods and systems of the present disclosure, the gas treatment unit 300 may be a conventional amine absorber system. In some aspects of the methods and systems of the present disclosure, the gas treatment unit 300 is fluidly coupled to the methanation subsystem (e.g., 101, 201). In some aspects of the methods and systems of the present disclosure, the gas treatment unit 300 is fluidly coupled to the methanation subsystem (e.g., 101, 201) and to the OCM subsystem (e.g., 103, 204).

With continued reference to FIG. 2, the system 200 includes a renewable $H_2$ subsystem 202 configured to generate a renewable $H_2$ feed stream 212. In the system 200 illustrated in FIG. 2, the renewable $H_2$ subsystem 202 comprises an electrolysis unit powered by electricity generated by a renewable energy source, such as wind, solar, biomass, geothermal, hydro-electric, nuclear, and combinations thereof. The electrolysis unit is disposed upstream of and fluidly coupled to the methanation subsystem 201 and to the OCM subsystem 204. The electrolysis unit receives a water stream 211 and converts the water to $H_2$ gas and $O_2$ gas via a water electrolysis reaction given by 2 $H_2O \rightarrow 2$ $H_2 + O_2$. The $H_2$ gas generated by the electrolysis reaction is directed to the methanation subsystem 201 as the renewable $H_2$ feed stream. Similarly, the $O_2$ gas generated by the electrolysis reaction is directed to the OCM subsystem 204 as at least a portion of the oxidant feed stream 214. In some aspects of the methods and systems of the present disclosure, the oxidant feed stream 214 directed to the OCM subsystem 204 consists of the renewable $O_2$ gas generated by the electrolysis reaction. Thus, the electrolysis unit can renewably supply all of the oxygen required for the oxidant feed stream 214 that is directed to the OCM subsystem 204. This aspect is particularly advantageous in that it can eliminate the need for an air separation unit (ASU), which is expensive and energy intensive, to supply oxygen to the OCM subsystem 204.

In the methanation subsystem 201, the carbon oxides (i.e., $CO_2$, CO, or both) in the carbon oxide feed stream 210 react with the $H_2$ from the renewable $H_2$ feed stream 212 to produce $CH_4$ via the following reactions: i) $CO_2 + 4$ $H_2 \rightarrow CH_4 + 2 H_2O$ and ii) $CO + 3 H_2 \rightarrow CH_4 + H_2O$. The $CH_4$ generated in the methanation subsystem 201 is directed to the OCM subsystem 204 as an OCM feed stream 213.

As can be appreciated by the methanation reactions listed above, such reactions can produce water, which can be present in the OCM feed stream 213 exiting the methanation subsystem 201. Accordingly, in some aspects of the methods and systems of the present disclosure, at least a portion of the $H_2O$ present in the OCM feed stream 213 may be removed prior to the OCM feed stream 213 being directed into the OCM subsystem 204. For example, the OCM feed stream 213 can be directed to a dehydration unit 203 to remove $H_2O$ from the OCM feed stream 213. The dehydration unit 203 may be a knock-out drum that removes $H_2O$ from the OCM feed stream 213 by cooling the OCM feed stream 213, or any other separation unit that is capable of removing the $H_2O$ from the OCM feed stream 213. In some aspects of the methods and systems of the present disclosure, the $H_2O$ removed from the OCM feed stream 213 can be recycled to the electrolysis unit via stream 222. On the other hand, if the OCM catalyst present in the OCM subsystem 204 is tolerant to the presence of steam, then the dehydration unit 203 can be omitted.

With continued reference to FIG. 2, the OCM feed stream 213 is directed to the OCM subsystem 204 along with the oxidant feed stream 214 to generate an OCM effluent 215 comprising $C_{2+}$ compounds including $C_2H_4$ and $C_2H_6$ and non-$C_{2+}$ impurities comprising one or more of CO, $CO_2$, $H_2$, and $CH_4$. The OCM effluent 215 can be directed to a separations subsystem 206 to separate the OCM effluent 215 into at least a first stream 217 comprising $CO_x$, $H_2$, and $CH_4$ and a second stream comprising $C_{2+}$ compounds including $C_2H_4$ and $C_2H_6$. As seen in FIG. 2, the first stream 217 comprising $CO_x$, $H_2$, and $CH_4$, or a portion thereof, can be recycled to the methanation subsystem 201 to facilitate generation of the OCM feed stream 213 via methanation. In accordance with some aspects of the methods and systems of the present disclosure, at least a portion of the first stream 217 may be purged to prevent the accumulation of inert components (e.g., $N_2$) in the system. In addition, the separations subsystem 206 can separate the second stream comprising $C_{2+}$ compounds into a third stream 218 comprising $C_2H_4$ product and a fourth stream 219 comprising $C_2H_6$. As shown in FIG. 2, the fourth stream 219 comprising $C_2H_6$ can be directed to the OCM subsystem 204 (e.g., to the OCM reactor or to the PBC unit) to produce additional $C_2H_4$ by cracking the $C_2H_6$. In accordance with some aspects of the methods and systems of the present disclosure, the electrolysis unit is fluidly coupled to the separations subsystem 206 and receives a stream 220 comprising $H_2O$ (connection not shown) that is separated or otherwise removed from the OCM effluent 215 by the separations subsystem 206.

The separations subsystem 206 may comprise any number of separation units or utilize any combination of separation technologies suitable for separating the products of an OCM reaction. For example, the separations subsystem 206 may separate the OCM effluent 215 with the aid of cryogenic separation, pressure swing adsorption, temperature swing adsorption, membrane separation, adsorbents, and combinations thereof. Examples of separations subsystems suitable for implementation in the methods and systems of the present disclosure are described in, for example, WO 2014/011646 A1, WO 2013/106771 A2, WO 2015/106023 A1, WO 2017/065947 A1, and WO 2018/118105 A1, the full disclosures of which are incorporated herein by reference in their entirety.

As seen in FIG. 2, in accordance with some aspects of the methods and systems of the present disclosure, the system 200 comprises a $CO_2$ removal unit 205 fluidly coupled to the OCM subsystem 204, the methanation subsystem 201, and the separations subsystem 206. The $CO_2$ removal unit 205 is configured to remove $CO_2$ from the OCM effluent 215, to direct at least a portion of the removed $CO_2$ to the methanation subsystem 201 via stream 216, and to direct the substantially $CO_2$-free OCM effluent to the separations subsystem 206. In accordance with some aspects of the methods and systems of the present disclosure, all of the $CO_2$ removed by the $CO_2$ removal unit 205 is directed to the methanation subsystem 201 via stream 216. The $CO_2$ removal unit 205 may comprise any known technology suitable for removing $CO_2$ from a process stream. Examples of suitable $CO_2$ removal technologies include, but are not limited to, an amine absorber system, pressure swing adsorption, temperature swing adsorption, membrane separation, solvent separation, and cryogenic separation.

While FIG. 2 illustrates a $CO_2$ removal unit 205 positioned downstream of the OCM subsystem 204 and upstream of the separations subsystem 206, it is contemplated that $CO_2$ contained in the OCM effluent 215 may be removed via the separations subsystem 206, thereby eliminating the need for the $CO_2$ removal unit 205. Such an arrangement would be particularly suitable in systems where the separations subsystem 206 is based on adsorption technology.

As described above, the system 200 for performing a method of converting carbon oxides to olefins illustrated in FIG. 2 utilizes a carbon oxide feed stream 210 as the primary or sole source of carbon fed into the system 200 along with a renewable hydrogen $H_2$ feed stream and a renewable oxidant feed stream generated by an electrolysis unit powered by a renewable energy source. The main reactions occurring for the overall process shown in FIG. 2 are as follows:

$$\text{Methanation: } CO_2 + 4H_2 \rightarrow CH_4 + 2H_2O$$

$$\text{Water Electrolysis: } 2H_2O \rightarrow 2H_2 + O_2$$

$$\text{OCM: } 2CH_4 + O_2 \rightarrow C_2H_4 + 2H_2O$$

As can be appreciated from the above reaction equations, it is clear that the electrolysis unit will produce $H_2$ and $O_2$ at a molar ratio of 2:1 (i.e., $2H_2:O_2$). Based on the methanation reaction and the OCM reaction, each mole of $CO_2$ fed into system (i.e., $CO_2$ via stream 210) will consume 4 moles of $H_2$ and 0.5 mole of $O_2$. Accordingly, much more $H_2$ is consumed in the process than $O_2$ and, thus, the excess $O_2$ will need to be purged from the process. In some aspects of the methods and systems of the present disclosure, the excess $O_2$ may be removed from the process/system and stored for later use or sold externally.

To bring the OCM reaction occurring in the OCM subsystem 204 into balance with the 2:1 ratio of $H_2$ to $O_2$ generated by the electrolysis unit, an optional makeup stream 221 comprising $CH_4$ may be directed to the OCM subsystem 204. It was determined that increasing the molar ratio of $CH_4$ to $CO_2$ fed into the system reduces the molar ratio of $H_2$ to $O_2$ consumption in the process. Estimated values of these molar ratios are shown in Table 1.

TABLE 1

| Effect of Molar Ratio of $CH_4:CO_2$ Fed on Molar Ratio of $H_2:O_2$ Consumed | |
| --- | --- |
| Molar Ratio of $CH_4:CO_2$ Fed | Molar Ratio of $H_2:O_2$ Consumed |
| 0:1 | 5.3:1 |
| 0.3:1 | 4.25:1 |
| 1:1 | 3:1 |
| 2.33:1 | 2.05:1 |

As can be appreciated by the data shown in Table 1, as a higher proportion of $CH_4$ is introduced into the system as compared to $CO_2$, the molar ratio of $H_2:O_2$ consumption decreases. Indeed, a molar ratio of 2.33:1 of $CH_4$ to $CO_2$ introduced into the system 200 results in a molar ratio of about 2:1 of $H_2$ to $O_2$ consumed in the system 200, which approximates the molar ratio of $H_2$ to $O_2$ generated by the electrolysis unit. Accordingly, in some aspects of the systems and methods of the present disclosure, an optional makeup stream 221 comprising $CH_4$ may be directed to the OCM subsystem 204 and a molar ratio of the $CH_4$ in the makeup stream to the $CO_2$ in the carbon oxide feed stream 210 (i.e., $CH_4$:$CO_2$) is from 0.01:1 to 5:1, including a molar ratio of $CH_4$:$CO_2$ of 0.1:1 to 4:1, a molar ratio of $CH_4$:$CO_2$ of 0.5:1 to 3.5:1, a molar ratio of $CH_4$:$CO_2$ of 0.75:1 to 3:1, and also including a molar ratio of $CH_4$:$CO_2$ of 1:1 to 2.5:1. Moreover, the ability to provide a source of $CH_4$ to the system 200 (e.g., via makeup stream 221) provides flexibility to operate the system 200 in the event that the supply of carbon oxides to the system 200 via the carbon oxide feed stream 210 fluctuates or is intermittent.

As noted above, when no $CH_4$ is fed to the system 200 excess $O_2$ will need to be purged from the system, but no $CO_2$ or other carbon emissions source is required to be emitted from the system 200. However, as $CH_4$ is fed via makeup stream 221 to the system 200 in increasing amounts (i.e., relative to the $CO_2$ fed to the system 200), some amount of $CO_2$ may need to be purged from the system 200 (e.g., via a purge stream off of stream 217), if for no other reason than to purge inert components such as $N_2$, which may be present as a minor impurity fed into the system (e.g., via the oxidant feed stream 214 and/or the optional makeup stream 221) and that would otherwise accumulate in the system 200 if not purged. In general, the amount of $CO_2$ required to be purged from the systems of the present disclosure is less than the amount of $CO_2$ fed into the system. Moreover, the $H_2$ and $O_2$ utilized in the methods and systems of the present disclosure are generated using renewable energy and resources that do not result in $CO_2$ emissions. Accordingly, the systems and methods of the present disclosure advantageously consume more $CO_2$ than is emitted and thereby produce olefins, such as $C_2H_4$ and $C_3H_6$, with negative carbon emissions, particularly negative $CO_2$ emissions.

Another advantage of the systems and methods of the present disclosure is that the systems and methods can be tailored to achieve a desired carbon efficiency. In some aspects of the systems and methods of the present disclosure, the systems and methods operate at a carbon efficiency of at least 90%, including at least 92%, at least 94%, at least 96%, at least 98%, and also including a carbon efficiency of at least 99%. In some aspects of the systems and methods of the present disclosure, the systems and methods operate at a carbon efficiency of 92% to 100%, including a carbon efficiency of 92% to 99.9%, a carbon efficiency of 93% to 99.9%, a carbon efficiency of 94% to 99.9%, a carbon efficiency of 95% to 99.9%, a carbon efficiency of 96% to 99.9%, a carbon efficiency of 97% to 99.9%, and also including a carbon efficiency of 99% to 99.9%. In OCM reactions, the carbon efficiency is typically determined based on the amount of carbon fed into the process from $CH_4$ that is converted to $C_{2+}$ compounds. However, in the systems and methods of the present disclosure, a carbon oxide feed stream (i.e., a feed stream comprising $CO_2$, CO, or both) is utilized as the primary or sole source of carbon fed into the system and, thus, the carbon efficiency based on the amount of carbon fed into the process from $CH_4$ will always be greater than 100%. For example, if the system 200 shown in FIG. 2 includes as feeds a makeup stream 221 comprising $CH_4$ and a carbon oxide feed stream 210 comprising $CO_2$, and the molar ratio of the $CH_4$ in the makeup stream to the $CO_2$ in the carbon oxide feed stream 210 (i.e., $CH_4$:$CO_2$) is 2.33:1, then the system 200 will produce 3.33 moles of carbon as $C_{2+}$ compounds. Thus, the system 200 will produce 3.33 moles of carbon as $C_{2+}$ compounds based on only 2.33 moles of carbon fed as $CH_4$, which translates to a carbon efficiency of about 143%.

Figure 4:
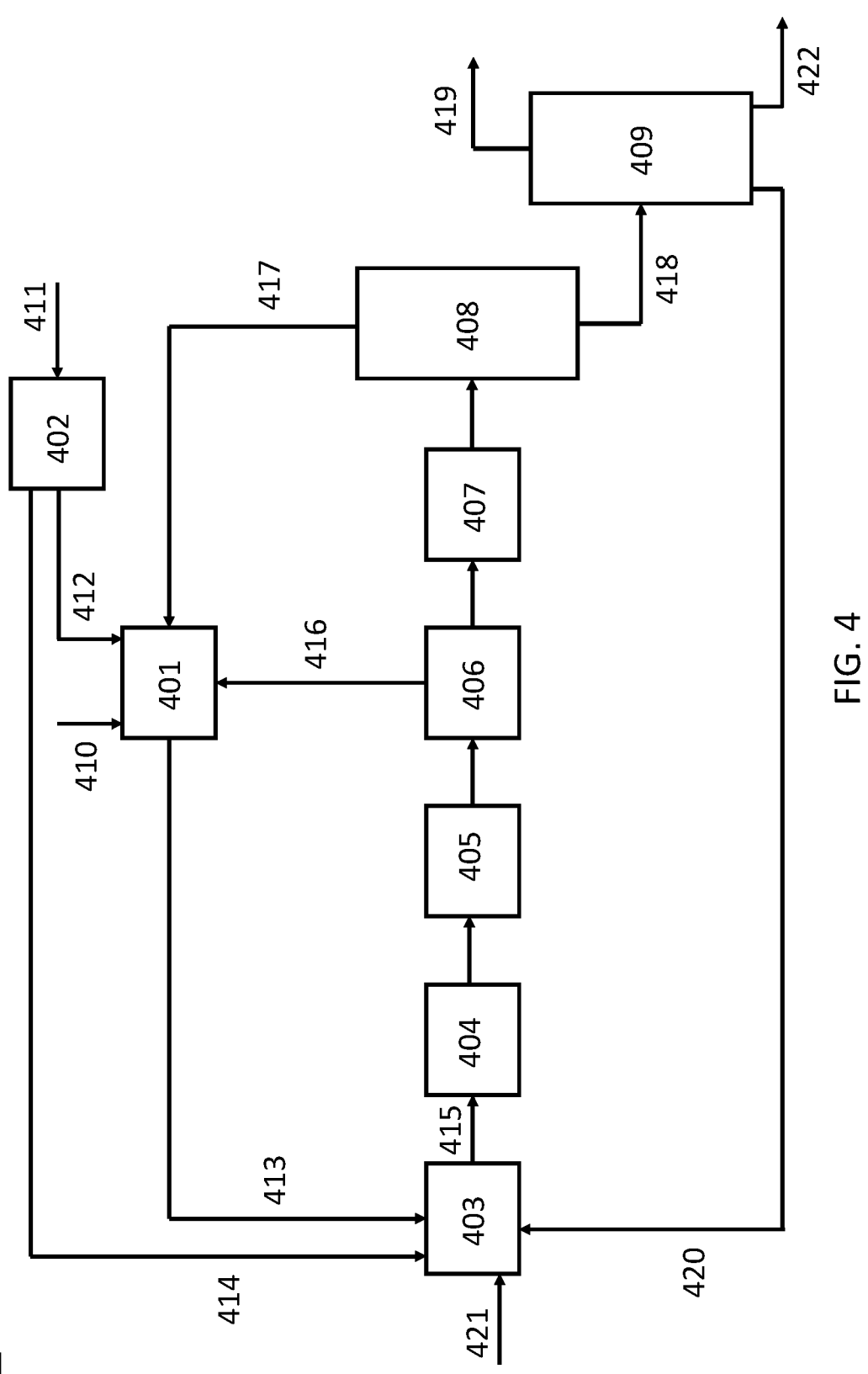
FIG. 4 illustrates a block flow diagram of a system for producing olefins, such as ethylene, from a carbon oxide feed stream in accordance with the present disclosure.

Referring now to FIG. 4, a block flow diagram of another implementation of a system 400 for performing a method of converting carbon oxides to olefins, including $C_2H_4$, in accordance with the present invention is shown. Similar to the system 200 illustrated in FIG. 2, the system 400 comprises a methanation subsystem 401, a renewable $H_2$ subsystem 402, an OCM subsystem 403, and a separations subsystem (not numbered). The methanation subsystem 401 is fluidly coupled to the renewable $H_2$ subsystem 402 and is configured to receive a carbon oxide feed stream 410 and a renewable $H_2$ feed stream 412 generated by the renewable $H_2$ subsystem 402 and to generate an OCM feed stream 213 comprising $CH_4$. The OCM subsystem 403 is downstream of and fluidly coupled to the methanation subsystem 401 and is configured to receive the OCM feed stream 413 and an oxidant feed stream 414 comprising $O_2$ to generate an OCM effluent 415 comprising $C_{2+}$ compounds including $C_2H_4$ and $C_2H_6$ and non-$C_{2+}$ impurities comprising one or more of CO, $CO_2$, $H_2$, and $CH_4$.

In the system 400 illustrated in FIG. 4, the methanation subsystem 401, the renewable $H_2$ subsystem 402, and the OCM subsystem 403 may be configured the same as the methanation subsystems 101, 201, the renewable $H_2$ subsystems 102, 202, and the OCM subsystems 103, 204 previously described with reference to FIGS. 1 and 2.

The OCM effluent 415 may be directed to one or more heat exchangers 404 to transfer heat from the OCM effluent 415 to a process stream and thereby cool the OCM effluent 415. In some aspects, the one or more heat exchangers may be a heat recovery steam generator (HRSG) that generates steam that may be used for heating, to generate power via a gas turbine, or for other processes.

With continued reference to FIG. 4, after passing through the one or more heat exchangers 404, the OCM effluent 415 may be directed to a process gas compressor 405 to increase the pressure of the OCM effluent 415 to a desired or suitable pressure such as at least about 100 psig (690 kPa), at least about 150 psig (1035 kPa), at least about 200 psig (1380 kPa), at least about 250 psig (1725 kPa), or at least about 300 psig (2070 kPa). The compressed OCM effluent 415 may be directed to a $CO_2$ removal unit 406 to remove $CO_2$ from the OCM effluent 415. At least a portion of the removed $CO_2$ may be directed to the methanation subsystem via stream 416. In accordance with some aspects of the methods and systems of the present disclosure, all of the $CO_2$ removed by the $CO_2$ removal unit 406 is directed to the methanation subsystem 401 via stream 416. The $CO_2$ removal unit 406 may be configured the same as the $CO_2$ removal unit 205 described above. The substantially $CO_2$-free OCM effluent 415 may be directed to a process gas dryer 407 to remove $H_2O$ from the substantially $CO_2$-free OCM effluent 415. The process gas dryer 407 may be one or more molecular sieve dryers or separator vessels to condense and separate the $H_2O$ from the substantially $CO_2$-free OCM effluent 415.

While FIG. 4 illustrates a $CO_2$ removal unit 406 positioned downstream of the OCM subsystem 403 and upstream of the separations subsystem, it is contemplated that $CO_2$ contained in the OCM effluent 415 may be removed via the separations subsystem, thereby eliminating the need for the $CO_2$ removal unit 406. Such an arrangement would be suitable in systems where the separations subsystem is based on adsorption technology.

Still referring to FIG. 4, after exiting the process gas dryer 407, the dry, substantially $CO_2$-free OCM effluent 415 may be directed to a separations subsystem that is downstream of and fluidly coupled to the OCM subsystem 403 and that comprises at least a demethanizer unit 408 and a $C_2$ purification unit 409. The demethanizer unit 408 is fluidly coupled to the methanation system 401 and to the $C_2$ purification unit 409, as illustrated in FIG. 4. The demethanizer unit 408 is configured to receive the OCM effluent 415, to separate the OCM effluent into a first stream 417 comprising $CO_x$, $H_2$, and $CH_4$ and a second stream 418 comprising $C_{2+}$ compounds including $C_2H_4$ and $C_2H_6$. At least a portion of the first stream 417 is directed from the demethanizer unit 408 to the methanation subsystem 401 to facilitate generation of the OCM feed stream 413 via methanation. In accordance with some aspects of the methods and systems of the present disclosure, all of the first stream 417 is recycled from the demethanizer unit 408 to the methanation subsystem to facilitate generation of the OCM feed stream 410 via methanation. In accordance with some aspects of the methods and systems of the present disclosure, at least a portion of the first stream 417 is purged to prevent the accumulation of inert components (e.g., $N_2$) in the system 400.

As shown in FIG. 4, the second stream 418 comprising $C_{2+}$ compounds including $C_2H_4$ and $C_2H_6$ may be directed to the $C_2$ purification unit 409. The $C_2$ purification unit 409 is fluidly coupled to the OCM subsystem 403 and is configured to receive the second stream 418 and to separate the second stream 418 into at least a third stream 419 comprising $C_2H_4$ and a fourth stream 420 comprising $C_2H_6$. The third stream 419 comprising $C_2H_4$ may be collected or directed to a downstream process that utilizes $C_2H_4$ as a feedstock. As seen in FIG. 4, the fourth stream 420 comprising $C_2H_6$ may be recycled to the OCM subsystem 403 (e.g., to an OCM reactor or to a PBC unit) to produce additional $C_2H_4$ by cracking the $C_2H_6$. In some aspects of the methods and systems of the present disclosure, the $C_2$ purification unit 409 may include a deethanizer unit (not shown) that is capable of separating $C_2$ compounds (e.g., ethane and ethylene) from $C_{3+}$ compounds (e.g., propane, propylene, butane, butene). Separated $C_{3+}$ compounds can leave the deethanizer unit along stream 422 and undergo additional downstream processing. The $C_2$ compounds from the deethanizer unit can be directed to a $C_2$ splitter (not shown), which can separate $C_2H_6$ from $C_2H_4$. The $C_2$ splitter can be a distillation column.

Figure 5:
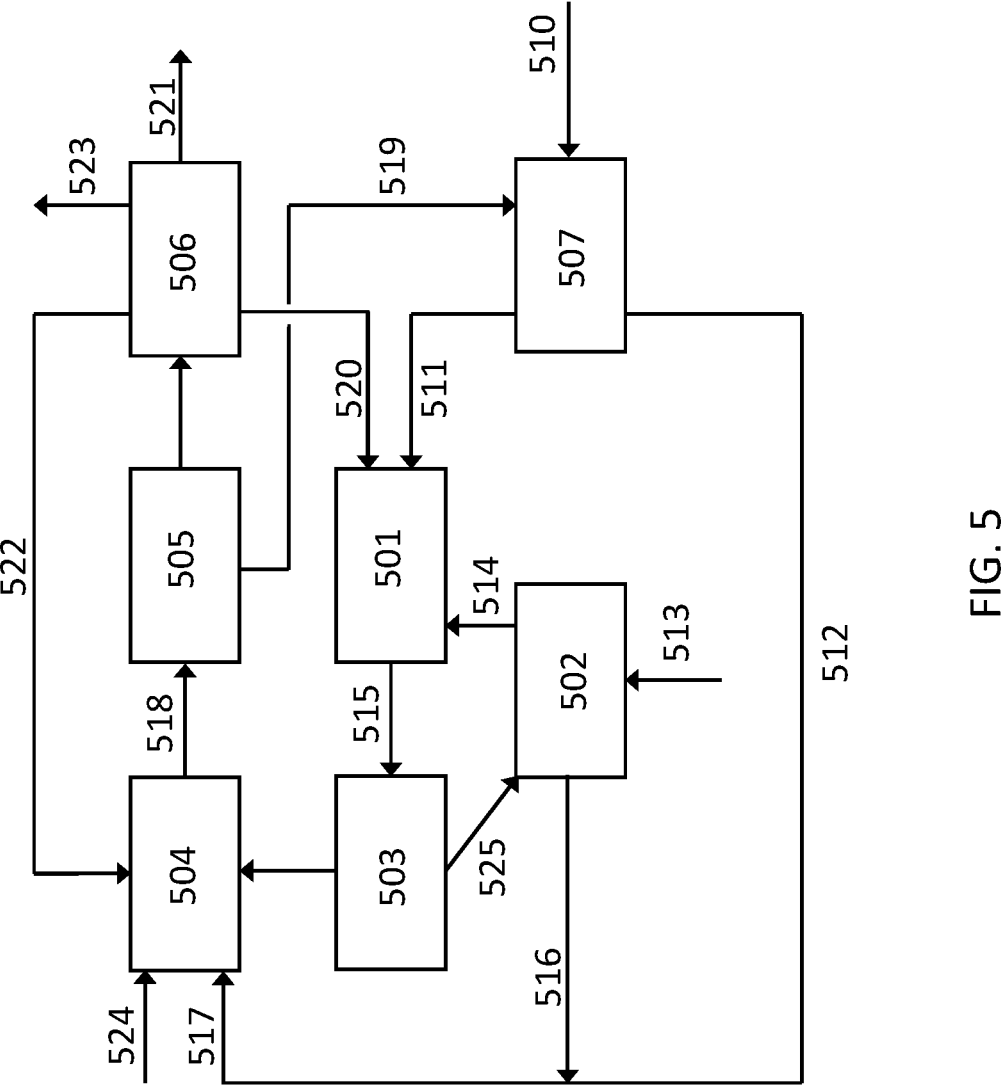
FIG. 5 illustrates a block flow diagram of a system for producing olefins, such as ethylene, from a carbon oxide feed stream in accordance with the present disclosure.

Referring now to FIG. 5, a block flow diagram of a system 500 for performing a method of converting carbon dioxide to olefins, including $C_2H_4$, in accordance with the present invention is shown. The system 500 comprises a methanation subsystem 501, a renewable $H_2$ subsystem 502, an OCM subsystem 504, a separations subsystem 506, and a $CO_2$ electrolysis unit 507. The $CO_2$ electrolysis unit 507 is configured to receive a feed stream 510 comprising $CO_2$ and to generate a first renewable electrolysis stream 511 comprising CO and a second renewable electrolysis stream 512 comprising $O_2$. The methanation subsystem 501 is fluidly coupled to the renewable $H_2$ subsystem 502 and the $CO_2$ electrolysis unit 507 and is configured to receive the first renewable electrolysis stream 511 and a renewable $H_2$ feed stream 514 generated by the renewable $H_2$ subsystem 502 and to generate an OCM feed stream 515 comprising $CH_4$. The OCM subsystem 504 is downstream of and fluidly coupled to the methanation subsystem 501 and the $CO_2$ electrolysis unit 507 and is configured to receive the OCM feed stream 515 and an oxidant feed stream 517 comprising the second renewable electrolysis stream 512 and to generate an OCM effluent 518 comprising $C_{2+}$ compounds including $C_2H_4$ and $C_2H_6$ and non-$C_{2+}$ impurities comprising one or more of CO, $CO_2$, $H_2$, and $CH_4$. The separations subsystem 506 is downstream of and fluidly coupled to the OCM subsystem 504 and is configured to receive the OCM effluent 518 and to separate the OCM effluent 518 into at least a first stream 520 comprising $CO_x$, $H_2$, and $CH_4$ and a second stream comprising $C_{2+}$ compounds including $C_2H_4$ and $C_2H_6$. The second stream may be further separated in the separations subsystem 506 to produce a third stream 521 comprising $C_2H_4$ and a fourth stream 522 comprising $C_2H_6$.

In the system 500 illustrated in FIG. 5, the methanation subsystem 501, the renewable $H_2$ subsystem 502, and the OCM subsystem 504 may have a configuration and include components similar to or the same as the methanation subsystem 101, the renewable $H_2$ subsystem 102, and the OCM subsystem 103 previously described herein with reference to FIG. 1. For example, the methanation subsystem 501 can include one or more methanation reactors that contain a methanation catalyst. The renewable $H_2$ subsystem 502 can comprise, for example, a water electrolysis unit that is powered by a renewable energy source. The OCM subsystem 504 can comprise, for example, one or more OCM reactors that include one or more OCM catalysts for facilitating an OCM reaction to generate the OCM effluent 518. The OCM subsystem 504 can also comprise a PBC unit.

As shown in FIG. 5, a feed stream 510 comprising $CO_2$ is directed to the $CO_2$ electrolysis unit 507. In accordance with the methods and systems of the present disclosure, the feed stream 510 comprising $CO_2$ is a primary or sole source of carbon fed into the system 500 or process. In accordance with some aspects of the methods and systems of the present disclosure, the feed stream 510 comprises captured $CO_2$. The captured $CO_2$ may be $CO_2$ that is captured from industrial facilities including, but not limited to, steel/metal production facilities, cement production facilities, coal-fired power plants, coal gasification, and biomass gasification. The captured $CO_2$ may also include some amount of CO. In accordance with some aspects of the methods and systems of the present disclosure, the feed stream 510 may comprise $CO_2$ that is generated by removing $CO_2$ from a natural gas stream, as previously described with respect to FIG. 3. In accordance with some aspects of the present disclosure, at least a portion of a substantially $CO_2$-free natural gas stream generated by a gas treatment unit, as described above with respect to FIG. 3, may be directed to the OCM subsystem 504 as a makeup stream 524 comprising $CH_4$.

As mentioned above, the $CO_2$ electrolysis unit 507 is configured to receive the feed stream 510 comprising $CO_2$ and to generate a first renewable electrolysis stream 511 comprising CO and a second renewable electrolysis stream 512 comprising $O_2$. The $CO_2$ electrolysis unit 507 is operable to convert $CO_2$ gas to CO gas and $O_2$ gas. For example, in certain aspects, the $CO_2$ electrolysis unit can convert the $CO_2$ gas to CO gas and $O_2$ gas in accordance with the following reaction: $CO_2 \rightarrow CO + \frac{1}{2} O_2$. The $CO_2$ electrolysis unit 507 can be based on any technology that can electrochemically convert $CO_2$ to CO and $O_2$. Such technologies include, but are not limited to, solid oxide electrolysis, molten carbonate electrolysis, and low-temperature electrolysis (e.g., an H-cell electrode or a gas-diffusion electrode). Technologies for electrochemically converting $CO_2$ to CO and $O_2$ are described, for example, in WO 2014/154253 A1 and U.S. Pat. No. 9,624,589 B2, the entire contents of which are incorporated by reference herein. In certain aspects of the methods and systems of the present disclosure, the $CO_2$ electrolysis unit 507 comprises a solid oxide electrolysis cell (SOEC). The SOEC may operate at temperatures of 500° C. to 1,200° C. The SOEC may comprise an electrolyte material including, but not limited to, a stabilized zirconia, such as yttria-stabilized zirconia (YSZ, a solid solution of $Y_2O_3$ and $ZrO_2$) or scandia-stabilized zirconia (ScSZ), and a doped ceria, such as gadolinia-doped ceria (CGO) or samaria-doped ceria. In addition, the SOEC may comprise a cathode material including, but not limited to, a composite of nickel and either YSZ or CGO. Furthermore, the SOEC may comprise an anode material including, but not limited to, doped perovskites of lanthanides and transition metals, such as Sr-doped $LaMnO_3$ (LSM), Sr-doped $La(Fe,Co)O_3$ (LSCF), or Sr-doped $SmCoO_3$ (SSC). The energy required to power the $CO_2$ electrolysis unit 507 to generate the first renewable electrolysis stream 511 and the second renewable electrolysis stream 512 may be provided by one or more renewable energy sources. Exemplary renewable energy sources that may be used in accordance with the methods and systems of the present disclosure include, but are not limited to, wind, solar, biomass, geothermal, hydro-electric, and nuclear.

As seen in FIG. 5, the first renewable electrolysis stream 511 is directed to the methanation subsystem 501 along with a renewable $H_2$ feed stream 514 generated by the renewable $H_2$ subsystem 502. In the system 500 illustrated in FIG. 5, the renewable $H_2$ subsystem 502 comprises a water electrolysis unit powered by electricity generated by a renewable energy source, such as wind, solar, biomass, geothermal, hydro-electric, nuclear, and combinations thereof. The water electrolysis unit is disposed upstream of and fluidly coupled to the methanation subsystem 501 and to the OCM subsystem 504. The water electrolysis unit receives a water stream 513 and converts the water to $H_2$ gas and $O_2$ gas via a water electrolysis reaction given by $2H_2O \rightarrow 2 H_2 + O_2$. The $H_2$ gas generated by the water electrolysis reaction is directed to the methanation subsystem 501 as the renewable $H_2$ feed stream 514. Similarly, the $O_2$ gas generated by the water electrolysis reaction is directed to the OCM subsystem 504 via stream 516 to form at least a portion of the oxidant feed stream 517. As seen in FIG. 5, stream 516 comprising $O_2$ formed the water electrolysis reaction can be combined with the second renewable electrolysis stream 512 to form the oxidant feed stream 517. In some aspects of the methods and systems of the present disclosure, the oxidant feed stream 517 directed to the OCM subsystem 504 consists of: i) the renewable $O_2$ gas stream 516 generated by the water electrolysis unit; and ii) the second renewable electrolysis stream 512. Thus, the water electrolysis unit and the $CO_2$ electrolysis unit can renewably supply all of the oxygen required for the oxidant feed stream 517 that is directed to the OCM subsystem 504. This aspect is particularly advantageous in that it can eliminate the need for an air separation unit (ASU), which is expensive and energy intensive, to supply oxygen to the OCM subsystem 504.

In the methanation subsystem 501, the carbon oxides (i.e., CO, $CO_2$, or both) in the first renewable electrolysis stream 511 react with $H_2$ from the renewable $H_2$ feed stream 514 to produce $CH_4$ via the following reactions: i) $CO_2 + 4 H_2 \rightarrow CH_4 + 2 H_2O$ and ii) $CO + 3 H_2 \rightarrow CH_4 + H_2O$. By providing a greater proportion of CO to the methanation subsystem 501 instead of $CO_2$ (as is achievable with the $CO_2$ electrolysis unit 507), less $H_2$ is required for the methanation reaction and less $H_2O$ is produced. In addition, a higher concentration of CO in the feed to the methanation subsystem 501 can reduce the size of the methanation reactor(s) and the amount of methanation catalyst required to perform the methanation reaction. The $CH_4$ generated in the methanation subsystem 501 is directed to the OCM subsystem 504 as an OCM feed stream 515.

As can be appreciated by the methanation reactions listed above, such reactions can produce water, which can be present in the OCM feed stream 515 exiting the methanation subsystem 501. Accordingly, in some aspects of the methods and systems of the present disclosure, at least a portion of the $H_2O$ present in the OCM feed stream 515 may be removed prior to the OCM feed stream 515 being directed into the OCM subsystem 504. For example, the OCM feed stream 515 can be directed to a dehydration unit 503 to remove $H_2O$ from the OCM feed stream 515. The dehydration unit 503 may be a knock-out drum that removes $H_2O$ from the OCM feed stream 515 by cooling the OCM feed stream 515, or any other separation unit that is capable of removing the $H_2O$ from the OCM feed stream 515. In some aspects of the methods and systems of the present disclosure, the $H_2O$ removed from the OCM feed stream 515 can be recycled to the water electrolysis unit via stream 525. On the other hand, if the OCM catalyst present in the OCM subsystem 504 is tolerant to the presence of steam, then the dehydration unit 503 can be omitted.

With continued reference to FIG. 5, the OCM feed stream 515 is directed to the OCM subsystem 504 along with the oxidant feed stream 517 comprising the second renewable electrolysis stream 512 to generate an OCM effluent 518 comprising $C_{2+}$ compounds including $C_2H_4$ and $C_2H_6$ and non-$C_{2+}$ impurities comprising one or more of CO, $CO_2$, $H_2$, and $CH_4$. The OCM effluent 518 can be directed to a separations subsystem 506 to separate the OCM effluent 518 into at least a first stream 520 comprising $CO_x$, $H_2$, and $CH_4$ and a second stream comprising $C_{2+}$ compounds including $C_2H_4$ and $C_2H_6$. As seen in FIG. 5, the first stream 520 comprising $CO_x$, $H_2$, and $CH_4$, or a portion thereof, can be recycled to the methanation subsystem 501 to facilitate generation of the OCM feed stream 515 via methanation. In accordance with some aspects of the methods and systems of the present disclosure, at least a portion of the first stream 520 may be purged to prevent the accumulation of inert components (e.g., $N_2$) in the system. In addition, the separations subsystem 506 can separate the second stream comprising $C_{2+}$ compounds into a third stream 521 comprising $C_2H_4$ product and a fourth stream 522 comprising $C_2H_6$. As shown in FIG. 5, the fourth stream 522 comprising $C_2H_6$ can be directed to the OCM subsystem 504 (e.g., to the OCM reactor or to the PBC unit) to produce additional $C_2H_4$ by cracking the $C_2H_6$. In accordance with some aspects of the methods and systems of the present disclosure, the water electrolysis unit is fluidly coupled to the separations subsystem 506 and receives a stream 523 comprising $H_2O$ (connection not shown) that is separated or otherwise removed from the OCM effluent 518 by the separations subsystem 506.

The separations subsystem 506 may comprise any number of separation units or utilize any combination of separation technologies suitable for separating the products of an OCM reaction. For example, the separations subsystem 506 may separate the OCM effluent 518 with the aid of cryogenic separation, pressure swing adsorption, temperature swing adsorption, membrane separation, adsorbents, and combinations thereof. Examples of separations subsystems suitable for implementation in the methods and systems of the present disclosure are described in, for example, WO 2014/011646 A1, WO 2013/106771 A2, WO 2015/106023 A1, WO 2017/065947 A1, and WO 2018/118105 A1, the full disclosures of which are incorporated herein by reference in their entirety.

As seen in FIG. 5, in accordance with some aspects of the methods and systems of the present disclosure, the system 500 comprises a $CO_2$ removal unit 505 fluidly coupled to the OCM subsystem 504, the $CO_2$ electrolysis unit 507, and the separations subsystem 506. The $CO_2$ removal unit 505 is configured to remove $CO_2$ from the OCM effluent 518, to direct at least a portion of the removed $CO_2$ to the $CO_2$ electrolysis unit 507 via stream 519, and to direct the substantially $CO_2$-free OCM effluent to the separations subsystem 506. In accordance with some aspects of the methods and systems of the present disclosure, all of the $CO_2$ removed by the $CO_2$ removal unit 505 is directed to the $CO_2$ electrolysis unit 507 via stream 519. The $CO_2$ removal unit 505 may comprise any known technology suitable for removing $CO_2$ from a process stream. Examples of suitable $CO_2$ removal technologies include, but are not limited to, an amine absorber system, pressure swing adsorption, temperature swing adsorption, membrane separation, solvent separation, and cryogenic separation.

While FIG. 5 illustrates a $CO_2$ removal unit 505 positioned downstream of the OCM subsystem 504 and upstream of the separations subsystem 506, it is contemplated that $CO_2$ contained in the OCM effluent 518 may be removed via the separations subsystem 506, thereby eliminating the need for the $CO_2$ removal unit 505. Such an arrangement would be suitable in systems where the separations subsystem 506 is based on adsorption technology.

Figure 6:
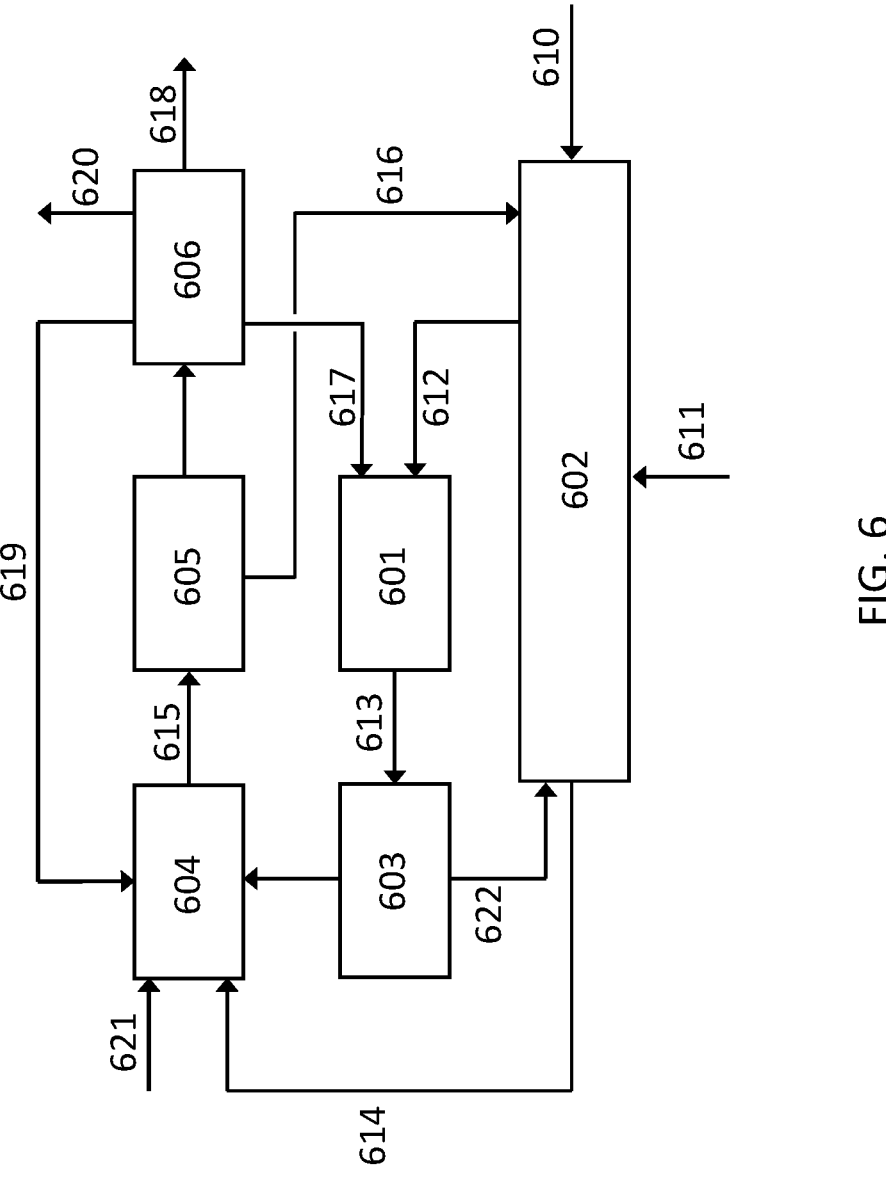
FIG. 6 illustrates a block flow diagram of a system for producing olefins, such as ethylene, from a carbon oxide feed stream in accordance with the present disclosure.

Referring now to FIG. 6, a block flow diagram of a system 600 for performing a method of converting carbon dioxide to olefins, including $C_2H_4$, in accordance with the present invention is shown. The system 600 comprises a methanation subsystem 601, a co-electrolysis unit 602, an OCM subsystem 604, and a separations subsystem 606. The co-electrolysis unit 602 is configured to receive a first feed stream 610 comprising $CO_2$ and a second feed stream comprising $H_2O$ and to generate a renewable syngas stream 612 comprising CO and $H_2$ and a renewable oxidant stream 614 comprising $O_2$. The methanation subsystem 601 is fluidly coupled to the co-electrolysis unit 602 and is configured to receive the renewable syngas stream 612 and to generate an OCM feed stream 613 comprising $CH_4$. The OCM subsystem 604 is downstream of and fluidly coupled to the methanation subsystem 601 and the co-electrolysis unit 602 and is configured to receive the OCM feed stream 613 and the renewable oxidant stream 614 and to generate an OCM effluent 615 comprising $C_{2+}$ compounds including $C_2H_4$ and $C_2H_6$ and non-$C_{2+}$ impurities comprising one or more of CO, $CO_2$, $H_2$, and $CH_4$. The separations subsystem 606 is downstream of and fluidly coupled to the OCM subsystem 604 and is configured to receive the OCM effluent 615 and to separate the OCM effluent 615 into at least a first stream 617 comprising $CO_x$, $H_2$, and $CH_4$ and a second stream comprising $C_{2+}$ compounds including $C_2H_4$ and $C_2H_6$. The second stream may be further separated in the separations subsystem 606 to produce a third stream 618 comprising $C_2H_4$ and a fourth stream 619 comprising $C_2H_6$.

In the system 600 illustrated in FIG. 6, the methanation subsystem 601 and the OCM subsystem 604 may have a configuration and include components similar to or the same as the methanation subsystem 101 and the OCM subsystem 103 previously described herein with reference to FIG. 1. For example, the methanation subsystem 601 can include one or more methanation reactors that contain a methanation catalyst. The OCM subsystem 604 can comprise, for example, one or more OCM reactors that include one or more OCM catalysts for facilitating an OCM reaction to generate the OCM effluent 615. The OCM subsystem 604 can also comprise a PBC unit.

As shown in FIG. 6, a first feed stream 610 comprising $CO_2$ and a second feed stream 611 comprising $H_2O$ are directed to the co-electrolysis unit 602. In accordance with the methods and systems of the present disclosure, the first feed stream 610 comprising $CO_2$ is a primary or sole source of carbon fed into the system 600 or process. In accordance with some aspects of the methods and systems of the present disclosure, the first feed stream 610 comprises captured $CO_2$. The captured $CO_2$ may be $CO_2$ that is captured from industrial facilities including, but not limited to, steel/metal production facilities, cement production facilities, coal-fired power plants, coal gasification, and biomass gasification. The captured $CO_2$ may also include some amount of CO. In accordance with some aspects of the methods and systems of the present disclosure, the first feed stream 610 may comprise $CO_2$ that is generated by removing $CO_2$ from a natural gas stream, as previously described with respect to FIG. 3. In accordance with some aspects of the present disclosure, at least a portion of a substantially $CO_2$-free natural gas stream generated by a gas treatment unit, as described above with respect to FIG. 3, may be directed to the OCM subsystem 604 as a makeup stream 621 comprising $CH_4$. In accordance with some aspects of the methods and systems of the present disclosure, the second feed stream 611 comprises steam.

As mentioned above, the co-electrolysis unit 602 is configured to receive the first and second feed streams 610, 611 and to generate a renewable syngas stream 612 comprising CO and $H_2$ and a renewable oxidant stream 614 comprising $O_2$. In certain aspects, the renewable oxidant stream 614 comprising $O_2$ is the sole source of $O_2$ supplied to the OCM subsystem 604. Thus, the co-electrolysis unit 602 can renewably supply all of the oxygen required for performing an OCM reaction in the OCM subsystem 604. This aspect is particularly advantageous in that it can eliminate the need for an air separation unit (ASU), which is expensive and energy intensive, to supply oxygen to the OCM subsystem 604. The co-electrolysis unit 602 is operable to convert $CO_2$ and water or steam to CO, $H_2$, and $O_2$. For example, in certain aspects, the co-electrolysis unit 602 can convert the $CO_2$ and water or steam to CO, $H_2$, and $O_2$ gas in accordance with the following reactions: $CO_2 \rightarrow CO + \frac{1}{2} O_2$ and $H_2O \rightarrow H_2 + \frac{1}{2} O_2$. The co-electrolysis unit 602 can be based on any technology that can electrochemically convert $CO_2$ and water or steam to syngas components CO and $H_2$, and $O_2$. One example of such technology is solid oxide electrolysis. Exemplary technologies that may be suitable for use in the co-electrolysis unit 602 of the present disclosure are described in U.S. Pat. No. 7,951,283 B2, U.S. Pat. No. 8,366,902 B2, and U.S. Pat. No. 9,631,284, the entire contents of which are incorporated by reference herein. In certain aspects of the methods and systems of the present disclosure, the co-electrolysis unit 602 comprises a solid oxide electrolysis cell (SOEC). The SOEC may operate at temperatures of 500° C. to 1,200° C. The SOEC may comprise an electrolyte material including, but not limited to, yttria stabilized zirconia electrolyte materials, scandia stabilized zirconia electrolyte materials, lanthanum gallate electrolyte materials (LSGM), ytterbium stabilized zirconia electrolyte materials, and ceria ($CeO_2$) electrolyte materials. The SOEC may include cathode materials conventionally used with solid oxide electrolysis cells including, but not limited to, a nickel-zirconia cermet material. The SOEC may include anode materials conventionally used with solid oxide electrolysis cells including, but not limited to, lanthanum strontium manganite or strontium doped lanthanum manganite materials. In certain aspects of the methods and systems of the present disclosure, the co-electrolysis unit 602 generates $CH_4$ in addition to the CO, $H_2$, and $O_2$. The energy required to power the co-electrolysis unit 602 to generate the renewable syngas stream 612 and the renewable oxidant stream 614 may be provided by one or more renewable energy sources. Exemplary renewable energy sources that may be used in accordance with the methods and systems of the present disclosure include, but are not limited to, wind, solar, biomass, geothermal, hydro-electric, and nuclear.

As seen in FIG. 6, the renewable syngas stream 612 is directed to the methanation subsystem 601. In the methanation subsystem 501, the carbon oxides (i.e., CO, $CO_2$, or both) and $H_2$ in the renewable syngas stream 612 react to produce $CH_4$ via the following reactions: i) $CO_2+4$ $H_2 \rightarrow CH_4+2 H_2O$ and ii) $CO+3H_2 \rightarrow CH_4+H_2O$. By providing a greater proportion of CO to the methanation subsystem 601 instead of $CO_2$ (as is achievable with the co-electrolysis unit 602), less $H_2$ is required for the methanation reaction and less $H_2O$ is produced. In addition, a higher concentration of CO in the feed to the methanation subsystem 601 can reduce the size of the methanation reactor(s) and the amount of methanation catalyst required to perform the methanation reaction. Furthermore, the $H_2$ generated by the co-electrolysis unit 602 can eliminate the need for a separate renewable $H_2$ subsystem. The $CH_4$ generated in the methanation subsystem 601 is directed to the OCM subsystem 604 as an OCM feed stream 613.

As can be appreciated by the methanation reactions listed above, such reactions can produce water, which can be present in the OCM feed stream 613 exiting the methanation subsystem 601. Accordingly, in some aspects of the methods and systems of the present disclosure, at least a portion of the $H_2O$ present in the OCM feed stream 613 may be removed prior to the OCM feed stream 613 being directed into the OCM subsystem 604. For example, the OCM feed stream 613 can be directed to a dehydration unit 603 to remove $H_2O$ from the OCM feed stream 613. The dehydration unit 603 may be a knock-out drum that removes $H_2O$ from the OCM feed stream 613 by cooling the OCM feed stream 613, or any other separation unit that is capable of removing the $H_2O$ from the OCM feed stream 613. In some aspects of the methods and systems of the present disclosure, the $H_2O$ removed from the OCM feed stream 613 can be recycled to the co-electrolysis unit 602 via stream 622. On the other hand, if the OCM catalyst present in the OCM subsystem 604 is tolerant to the presence of steam, then the dehydration unit 603 can be omitted.

With continued reference to FIG. 6, the OCM feed stream 613 is directed to the OCM subsystem 604 along with the renewable oxidant stream 614 to generate an OCM effluent 615 comprising $C_{2+}$ compounds including $C_2H_4$ and $C_2H_6$ and non-$C_{2+}$ impurities comprising one or more of CO, $CO_2$, $H_2$, and $CH_4$. The OCM effluent 615 can be directed to a separations subsystem 606 to separate the OCM effluent 615 into at least a first stream 617 comprising $CO_x$, $H_2$, and $CH_4$ and a second stream comprising $C_{2+}$ compounds including $C_2H_4$ and $C_2H_6$. As seen in FIG. 6, the first stream 617 comprising $CO_x$, $H_2$, and $CH_4$, or a portion thereof, can be recycled to the methanation subsystem 601 to facilitate generation of the OCM feed stream 613 via methanation. In accordance with some aspects of the methods and systems of the present disclosure, at least a portion of the first stream 617 may be purged to prevent the accumulation of inert components (e.g., $N_2$) in the system. In addition, the separations subsystem 606 can separate the second stream comprising $C_{2+}$ compounds into a third stream 618 comprising $C_2H_4$ product and a fourth stream 619 comprising $C_2H_6$. As shown in FIG. 6, the fourth stream 619 comprising $C_2H_6$ can be directed to the OCM subsystem 604 (e.g., to the OCM reactor or to the PBC unit) to produce additional $C_2H_4$ by cracking the $C_2H_6$. In accordance with some aspects of the methods and systems of the present disclosure, the co-electrolysis unit is fluidly coupled to the separations subsystem 606 and receives a stream 620 comprising $H_2O$ (connection not shown) that is separated or otherwise removed from the OCM effluent 615 by the separations subsystem 606.

The separations subsystem 606 may comprise any number of separation units or utilize any combination of separation technologies suitable for separating the products of an OCM reaction. For example, the separations subsystem 606 may separate the OCM effluent 615 with the aid of cryogenic separation, pressure swing adsorption, temperature swing adsorption, membrane separation, adsorbents, and combinations thereof. Examples of separations subsystems suitable for implementation in the methods and systems of the present disclosure are described in, for example, WO 2014/011646 A1, WO 2013/106771 A2, WO 2015/106023 A1, WO 2017/065947 A1, and WO 2018/118105 A1, the full disclosures of which are incorporated herein by reference in their entirety.

As seen in FIG. 6, in accordance with some aspects of the methods and systems of the present disclosure, the system 600 comprises a $CO_2$ removal unit 605 fluidly coupled to the OCM subsystem 604, the co-electrolysis unit 602, and the separations subsystem 606. The $CO_2$ removal unit 605 is configured to remove $CO_2$ from the OCM effluent 615, to direct at least a portion of the removed $CO_2$ to the co-electrolysis unit 602 via stream 616, and to direct substantially $CO_2$-free OCM effluent to the separations subsystem 606. In accordance with some aspects of the methods and systems of the present disclosure, all of the $CO_2$ removed by the $CO_2$ removal unit 605 is directed to the $CO_2$ electrolysis unit 507 via stream 519. The $CO_2$ removal unit 605 may comprise any known technology suitable for removing $CO_2$ from a process stream. Examples of suitable $CO_2$ removal technologies include, but are not limited to, an amine absorber system, pressure swing adsorption, temperature swing adsorption, membrane separation, solvent separation, and cryogenic separation.

While FIG. 6 illustrates a $CO_2$ removal unit 605 positioned downstream of the OCM subsystem 604 and upstream of the separations subsystem 606, it is contemplated that $CO_2$ contained in the OCM effluent 615 may be removed via the separations subsystem 606, thereby eliminating the need for the $CO_2$ removal unit 605. Such an arrangement would be suitable in systems where the separations subsystem 606 is based on adsorption technology.

Although the figures may illustrate various streams being introduced separately into a unit, it is contemplated that two or more of the streams being introduced into a unit may be combined or mixed into a single stream before being introduced into the unit. For example, carbon oxide feed stream 410 and stream 416 comprising $CO_2$ illustrated in FIG. 4 may be combined and fed into the methanation subsystem 401 as a single stream.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

All ranges and parameters, including but not limited to percentages, parts, and ratios, disclosed herein are understood to encompass any and all sub-ranges assumed and subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more (e.g., 1 to 6.1), and ending with a maximum value of 10 or less (e.g., 2.3 to 9.4, 3 to 8, 4 to 7), and finally to each number 1, 2, 3, 4, 5, 6, 7, 8, 9, and 10 contained within the range.

The methods and systems of the present disclosure can comprise, consist of, or consist essentially of the essential elements and limitations of the disclosure as described herein, as well as any additional or optional components or features described herein or otherwise known to be useful in hydrocarbon or petrochemical processing applications, including oxidative coupling of methane applications.

To the extent that the terms "include," "includes," or "including" are used in the specification or the claims, they are intended to be inclusive in a manner similar to the term "comprising" as that term is interpreted when employed as a transitional word in a claim. Furthermore, to the extent that the term "or" is employed (e.g., A or B), it is intended to mean "A or B or both A and B." When the Applicant intends to indicate "only A or B but not both," then the term "only A or B but not both" will be employed. Thus, use of the term "or" herein is the inclusive, and not the exclusive use. Furthermore, the phrase "at least one of A, B, and C" should be interpreted as "only A or only B or only C or any combinations thereof." In the present disclosure, the words "a" or "an" are to be taken to include both the singular and the plural. Conversely, any reference to plural items shall, where appropriate, include the singular.

In accordance with the present disclosure, it is possible to utilize the various inventive concepts in combination with one another. Additionally, any particular feature recited as relating to a particularly disclosed aspect of the methods and systems of the present disclosure should be interpreted as available for use with all disclosed aspects of the methods and systems of the present disclosure, unless incorporation of the particular feature would be contradictory to the express terms of the disclosed aspect. Additional advantages and modifications will be readily apparent to those skilled in the art. Therefore, the disclosure, in its broader aspects, is not limited to the specific details presented therein, the representative apparatus, or the illustrative examples shown and described. Accordingly, departures may be made from such details without departing from the spirit or scope of the general inventive concepts.

The scope of the general inventive concepts presented herein are not intended to be limited to the particular exemplary aspects shown and described herein. From the disclosure given, those skilled in the art will not only understand the general inventive concepts and their attendant advantages, but will also find apparent various changes and modifications to the devices, systems, and methods disclosed. It is sought, therefore, to cover all such changes and modifications as fall within the spirit and scope of the general inventive concepts, as described and/or claimed herein, and any equivalents thereof.

What is claimed is:

1. A method of converting carbon oxides to olefins including ethylene ($C_2H_4$), the method comprising:
 (a) directing a renewable hydrogen ($H_2$) feed stream and a carbon oxide feed stream comprising carbon dioxide ($CO_2$), carbon monoxide (CO), or both $CO_2$ and CO to a methanation reactor to generate an oxidative coupling of methane (OCM) feed stream comprising methane ($CH_4$); and
 (b) directing the OCM feed stream and an oxidant feed stream comprising oxygen ($O_2$) to an OCM reactor comprising an OCM catalyst and performing an OCM reaction to generate an OCM effluent comprising (i) $C_{2+}$ compounds including $C_2H_4$ and ethane ($C_2H_6$) and (ii) non-$C_{2+}$ impurities comprising one or more of CO, $CO_2$, $H_2$, and $CH_4$,
 wherein the method produces olefins including C2H4 with negative carbon emissions,
 wherein the carbon oxide feed stream is a sole source of carbon utilized in the method, and
 wherein the method achieves a carbon efficiency based on the amount of carbon fed into the process from $CH_4$ of greater than 100%.

2. The method of claim 1, wherein the renewable $H_2$ feed stream is generated by at least one of: (i) water electrolysis; (ii) biomass gasification; (iii) ammonia cracking; or (iv) hydrogen sulfide decomposition.

3. The method of claim 2, wherein the renewable $H_2$ feed stream is generated by water electrolysis, and wherein the water electrolysis generates renewable $O_2$ that is used as at least a portion of the oxidant feed stream.

4. The method of claim 3, further comprising removing water from the OCM feed stream and directing the water to an electrolysis unit for performing the water electrolysis.

5. The method of claim 1, further comprising separating the OCM effluent into at least (i) a first stream comprising $CO_x$, $H_2$, and $CH_4$ and (ii) a second stream comprising $C_{2+}$ compounds including $C_2H_4$ and $C_2H_6$; and
 directing at least a portion of the first stream to the methanation reactor.

6. The method of claim 1, further comprising removing $CO_2$ from the OCM effluent and directing at least a portion of the removed $CO_2$ to the methanation reactor.

7. The method of claim 5, further comprising separating the second stream to produce a third stream comprising $C_2H_4$ and a fourth stream comprising $C_2H_6$; and
 directing the fourth stream to a post-bed cracking unit downstream of the OCM catalyst.

8. The method of claim 1, further comprising directing a makeup stream comprising $CH_4$ to the OCM reactor, wherein a molar ratio of the $CH_4$ in the makeup stream to the $CO_2$ in the carbon oxide feed stream is from 0.01:1 to 5:1.

9. The method of claim 1, wherein the carbon oxide feed stream comprises captured $CO_2$.

10. A method of converting carbon dioxide to olefins including ethylene ($C_2H_4$), the method comprising:
 (a) directing a natural gas stream containing carbon dioxide ($CO_2$) to a gas treatment unit to generate a $CO_2$ feed stream and a substantially $CO_2$-free natural gas stream;
 (b) directing a renewable hydrogen ($H_2$) feed stream and the $CO_2$ feed stream to a methanation reactor to generate an oxidative coupling of methane (OCM) feed stream comprising methane ($CH_4$); and
 (c) directing the OCM feed stream and an oxidant feed stream comprising oxygen ($O_2$) to an OCM reactor comprising an OCM catalyst and performing an OCM reaction to generate an OCM effluent comprising (i) $C_{2+}$ compounds including $C_2H_4$ and ethane ($C_2H_6$) and (ii) non-$C_{2+}$ impurities comprising one or more of CO, $CO_2$, $H_2$, and $CH_4$,
 wherein the method produces olefins including $C_2H_4$ with negative carbon emissions.

11. The method of claim 10, wherein the renewable $H_2$ feed stream is generated by at least one of: (i) water electrolysis; (ii) biomass gasification; (iii) ammonia cracking; or (iv) hydrogen sulfide decomposition.

12. The method of claim 11, wherein the renewable $H_2$ feed stream is generated by water electrolysis, and wherein the water electrolysis generates renewable $O_2$ that is used as at least a portion of the oxidant feed stream.

13. The method of claim 12, further comprising removing water from the OCM feed stream and directing the water to an electrolysis unit for performing the water electrolysis.

14. The method of claim 10, further comprising separating the OCM effluent into at least (i) a first stream comprising $CO_x$, $H_2$, and $CH_4$ and (ii) a second stream comprising $C_{2+}$ compounds including $C_2H_4$ and $C_2H_6$; and directing at least a portion of the first stream to the methanation reactor.

15. The method of claim 10, further comprising removing $CO_2$ from the OCM effluent and directing at least a portion of the removed $CO_2$ to the methanation reactor.

16. The method of claim 14, further comprising separating the second stream to produce a third stream comprising $C_2H_4$ and a fourth stream comprising $C_2H_6$; and directing the fourth stream to a post-bed cracking unit downstream of the OCM catalyst.

17. The method of claim 10, further comprising directing a makeup stream comprising at least a portion of the substantially $CO_2$-free natural gas stream to the OCM reactor, wherein a molar ratio of $CH_4$ in the makeup stream to $CO_2$ in the $CO_2$ feed stream is from 0.01:1 to 5:1.

18. The method of claim 10, further comprising adding a source of captured $CO_2$ to the $CO_2$ feed stream.

19. A method of converting carbon oxides to olefins including ethylene ($C_2H_4$), the method comprising:

(a) directing a renewable hydrogen ($H_2$) feed stream and a carbon oxide feed stream comprising carbon dioxide ($CO_2$), carbon monoxide (CO), or both $CO_2$ and CO to a methanation reactor to generate an oxidative coupling of methane (OCM) feed stream comprising methane ($CH_4$); and (b) directing the OCM feed stream and an oxidant feed stream comprising oxygen ($O_2$) to an OCM reactor comprising an OCM catalyst and performing an OCM reaction to generate an OCM effluent comprising (i) $C_{2+}$ compounds including $C_2H_4$ and ethane ($C_2H_6$) and (ii) non-$C_{2+}$ impurities comprising one or more of CO, $CO_2$, $H_2$, and $CH_4$, wherein the method produces olefins including $C_2H_4$ with negative carbon emissions, and wherein the carbon oxide feed stream is a sole source of carbon utilized in the method.

\* \* \* \* \*